United States Patent [19]

Baird et al.

[11] Patent Number: 4,908,247

[45] Date of Patent: Mar. 13, 1990

[54] ARTICLE INCLUDING SEGMENT WHICH IS ELASTICALLY SHIRRABLE AFTER MANUFACTURE

[75] Inventors: James C. Baird, Cincinnati; Thurman J. Koger, II, Hamilton; Delmar R. Muckenfuhs, Middletown; Milton D. Spahni, Okeana, all of Ohio

[73] Assignee: The Procter & Gamble Company, Cincinnati, Ohio

[21] Appl. No.: 36,941

[22] Filed: Apr. 10, 1987

Related U.S. Application Data

[63] Continuation-in-part of Ser. No. 852,053, Apr. 15, 1986, abandoned.

[51] Int. Cl.$^4$ .......................... A41B 9/14; A41B 13/02; A41F 9/02; A41F 13/16; B32B 31/16
[52] U.S. Cl. ........................................ 428/34.9; 2/76; 2/78 C; 2/221; 2/237; 2/401; 5/496; 5/497; 24/16 PB; 24/30.5 P; 112/262.1; 112/262.2; 156/73.1; 156/85; 156/86; 156/92; 156/93; 156/155; 156/161; 156/163; 156/164; 156/211; 156/249; 156/252; 156/256; 156/290; 156/291; 428/202; 428/212; 428/217; 428/910; 428/36.8; 428/76; 428/101; 428/102; 428/110; 428/132; 428/135; 428/138; 428/142; 428/152; 428/161; 428/162; 428/172; 428/192; 428/195; 428/196; 493/962; 604/385.2; 383/71; 383/112; 383/116; 383/118
[58] Field of Search ................... 2/237, 76, 78 C, 221, 2/401; 112/262.1, 262.3; 604/385.2; 156/85, 161, 164, 155, 249, 73.1, 86, 92, 93, 163, 211, 252, 256, 290, 291; 428/196, 195, 35, 36, 76, 101, 102, 110, 132, 135, 138, 142, 152, 161, 162, 172, 192, 196, 202, 212, 217, 910; 383/71, 112, 116, 118; 493/962; 5/496, 497

[56] References Cited

U.S. PATENT DOCUMENTS

| 375,073 | 12/1887 | Kayser . | |
|---|---|---|---|
| 783,726 | 9/1857 | Neyret et al. | 2/237 |
| 2,068,456 | 1/1937 | Hooper | 154/2 |

(List continued on next page.)

FOREIGN PATENT DOCUMENTS

| WO86/00676 | 4/1980 | PCT Int'l Appl. . |
|---|---|---|
| 1324591 | 7/1973 | United Kingdom . |
| 1389201 | 4/1975 | United Kingdom . |
| 2056910 | 3/1981 | United Kingdom . |
| 2160473 | 5/1984 | United Kingdom . |

Primary Examiner—James C. Cannon
Attorney, Agent, or Firm—E. Kelly Linman; John V. Gorman; Richard C. Witte

[57] ABSTRACT

An article including at least one segment which is capable of being elastically shirred along at least a portion of its length subsequent to manufacture of the article, preferably by mechanical manipulation of a predetermined portion of the elastically shirrable segment. The predetermined mechanically manipulatable portion of the elastically shirrable segment preferably comprises an elastomeric monomer which is maintained in a prestretched and tensioned condition in the desired direction of shirring. The opposed ends of the elastically shirrable segment in the article are interconnected to one another through the prestretched and tensioned elastomeric member. The prestretched and tensioned elastomeric member is also secured in fixed relation to at least one rigidifying member to form a composite structure which is strong enough to resist collapse in a direction parallel to the tensile forces acting upon the prestretched and tensioned elastomeric member prior to mechanical manipulation of the composite structure. The article is elastically shirred by mechanically manipulating the predetermined portion of the shirrable segment until movement of the prestretched and tensioned elastomeric member relative to the rigidifying member is effected. To elasticize the article containing the elastically shirrable segment, the relative movement between the prestretched and tensioned elastomeric member and the rigidifying member must be sufficient to release the tensile forces in the mechanically manipulated portion of the composite structure. This relative movement produces a degree of elastic shirring in the segment, and consequently in the article to which it is attached, in the direction of prestretching of the elastomeric member. The degree of segment shirring is proportional to the extent to which there is relative movement between the prestretched and tensioned elastomeric member and the rigidifying member in the area comprising the composite structure. Thus, the tension in the elastically shirrable segment can be increased by the user, as desired, by mechanically manipulating more of the composite structure.

Elastically shirrable segments of the present invention are particularly well suited to high speed article manufacturing operations, since the segments can be applied to the articles in a substantially untensioned condition and their tension released subsequent to article manufacture.

71 Claims, 11 Drawing Sheets

U.S. PATENT DOCUMENTS

| | | | |
|---|---|---|---|
| 2,157,463 | 5/1939 | Shepherd | 57/140 |
| 2,301,222 | 11/1942 | Minich | 18/57 |
| 2,307,020 | 1/1943 | Copeman | 154/2 |
| 2,451,016 | 10/1948 | Alderfer | 154/91 |
| 2,803,056 | 8/1957 | Brissey, Jr. et al. | 29/450 |
| 2,966,439 | 12/1960 | Sorel | 154/39 |
| 2,993,820 | 7/1961 | Marshall | 154/2.27 |
| 3,315,328 | 4/1967 | Ibrahim | 28/72 |
| 3,319,328 | 5/1967 | Finger et al. | 29/423 |
| 3,396,460 | 8/1968 | Wetmore | 29/629 |
| 3,448,478 | 6/1969 | Nash et al. | 15/104.93 |
| 3,474,517 | 10/1969 | Menne | 29/427 |
| 3,515,798 | 6/1970 | Sievert | 174/135 |
| 3,607,602 | 9/1971 | Greskiewicz | 161/160 |
| 3,620,896 | 11/1971 | Glasgow | 161/123 |
| 3,620,898 | 11/1971 | Harris et al. | 161/160 |
| 3,639,917 | 2/1972 | Althouse | 2/270 |
| 3,669,824 | 6/1972 | Hess | 161/166 |
| 3,694,815 | 10/1972 | Burger | 2/224 |
| 3,770,556 | 11/1973 | Evans et al. | 161/160 |
| 3,794,549 | 2/1974 | Schroteler | 161/43 |
| 3,819,401 | 6/1974 | Massengale et al. | 156/85 |
| 3,824,331 | 7/1974 | Mixon, Jr. et al. | 174/135 |
| 3,898,369 | 8/1975 | Clabburn | 174/36 |
| 3,912,565 | 10/1975 | Koch et al. | 156/85 |
| 3,920,018 | 11/1975 | Schaar | 128/287 |
| 3,946,480 | 3/1976 | Dienes | 29/235 |
| 4,023,571 | 5/1977 | Comerford et al. | 128/290 |
| 4,026,985 | 5/1977 | Rasmussen | 264/129 |
| 4,035,534 | 7/1977 | Nyberg | 428/36 |
| 4,036,233 | 7/1977 | Kozak | 128/287 |
| 4,041,949 | 8/1977 | Kozak | 128/287 |
| 4,050,462 | 9/1977 | Woon et al. | 128/287 |
| 4,070,746 | 1/1978 | Evans et al. | 29/450 |
| 4,081,301 | 3/1978 | Buell | 156/164 |
| 4,126,238 | 11/1978 | Rausing | 215/1 |
| 4,135,553 | 1/1979 | Evans et al. | 138/141 |
| 4,179,320 | 12/1979 | Midgley et al. | 156/86 |
| 4,246,900 | 1/1981 | Schroder | 128/287 |
| 4,259,220 | 3/1981 | Bunnelle et al. | 260/27 |
| 4,287,012 | 9/1981 | Midgley et al. | 156/86 |
| 4,300,562 | 11/1981 | Pieniak | 128/287 |
| 4,326,904 | 4/1982 | Eckert et al. | 156/85 |
| 4,333,978 | 6/1982 | Kocher | 156/164 |
| 4,338,970 | 7/1982 | Krackeler et al. | 138/141 |
| 4,352,355 | 10/1982 | Mesek et al. | 128/287 |
| 4,388,075 | 6/1983 | Mesek et al. | 604/385 |
| 4,389,212 | 6/1983 | Tritsch | 604/389 |
| 4,392,898 | 7/1983 | Pithouse et al. | 156/85 |
| 4,407,284 | 10/1983 | Pieniak | 604/385 |
| 4,425,390 | 1/1984 | Changani et al. | 428/43 |
| 4,447,240 | 5/1984 | Ito et al. | 604/385 |
| 4,450,026 | 5/1984 | Pieniak et al. | 156/164 |
| 4,486,366 | 12/1984 | Reddy | 264/25 |
| 4,487,643 | 12/1984 | Ellett | 156/80 |
| 4,507,163 | 3/1985 | Menard | 156/164 |
| 4,525,407 | 6/1985 | Ness | 428/138 |
| 4,527,990 | 7/1985 | Sigl | 604/385 |
| 4,543,099 | 9/1985 | Bunnelle et al. | 604/385 |
| 4,547,243 | 10/1985 | Brody | 156/164 |
| 4,552,795 | 11/1985 | Hansen et al. | 428/110 |
| 4,556,596 | 12/1985 | Meuli | 428/152 |
| 4,573,991 | 3/1986 | Pieniak et al. | 604/285 |
| 4,578,133 | 3/1986 | Oshefsky et al. | 156/164 |
| 4,585,607 | 4/1986 | Krackeler et al. | 264/229 |
| 4,630,320 | 12/1986 | Van Gompel | 2/406 |
| 4,640,859 | 2/1987 | Hansen et al. | 428/105 |
| 4,675,016 | 6/1987 | Meuli et al. | 604/385 |

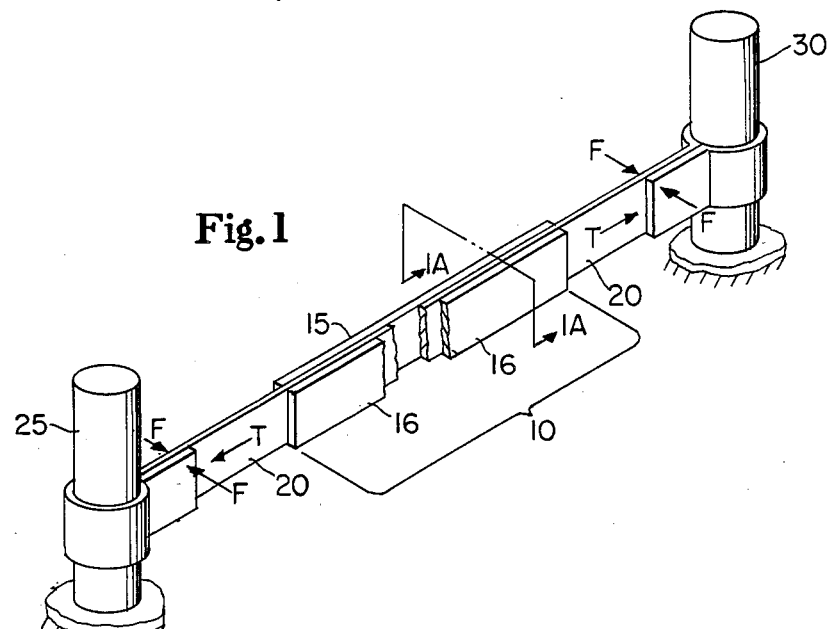
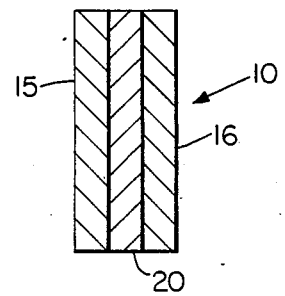
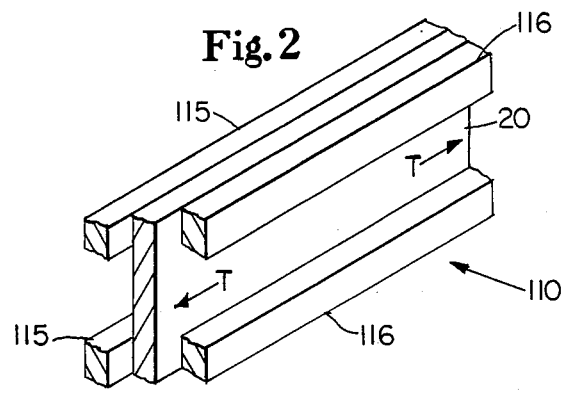

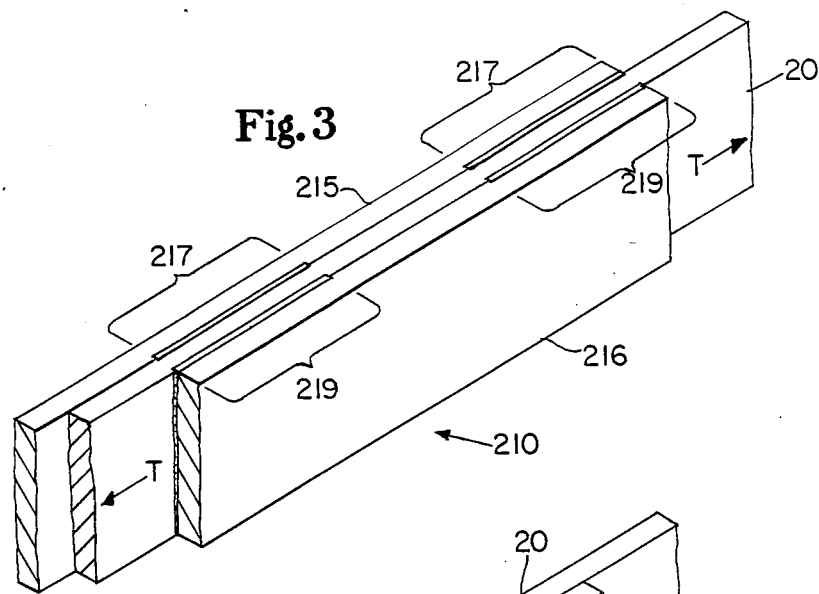
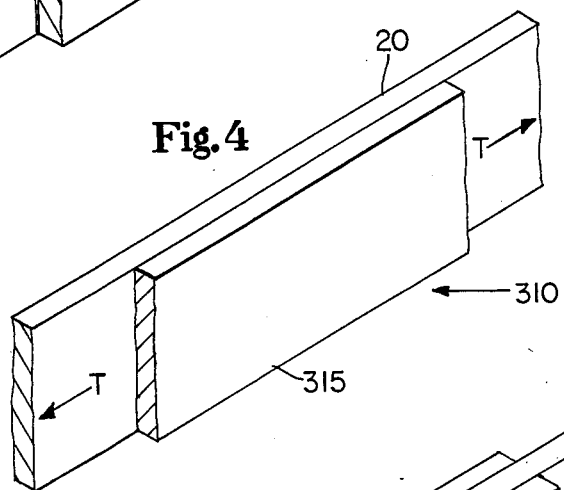
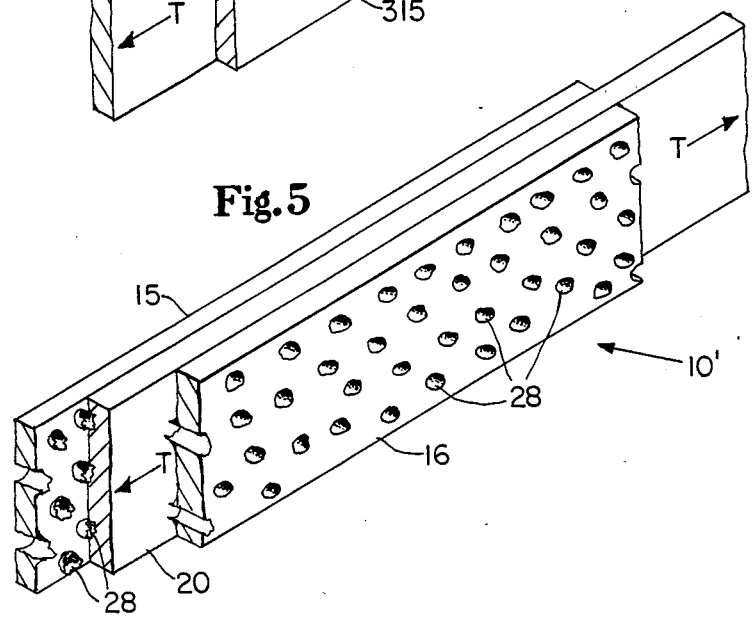

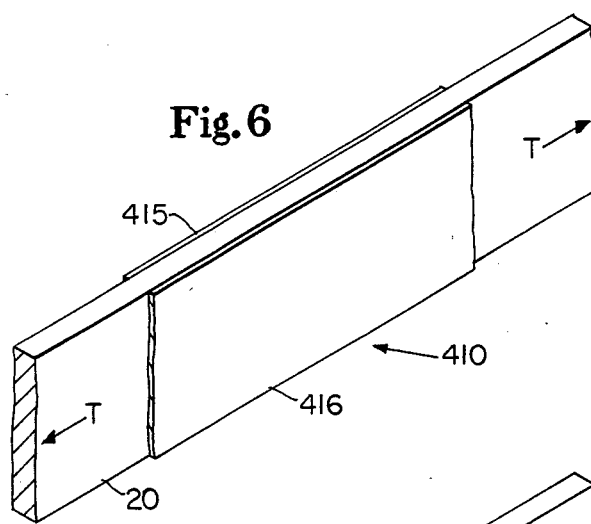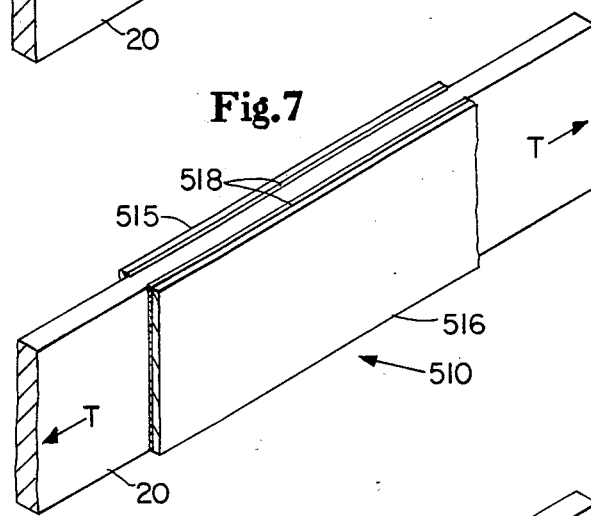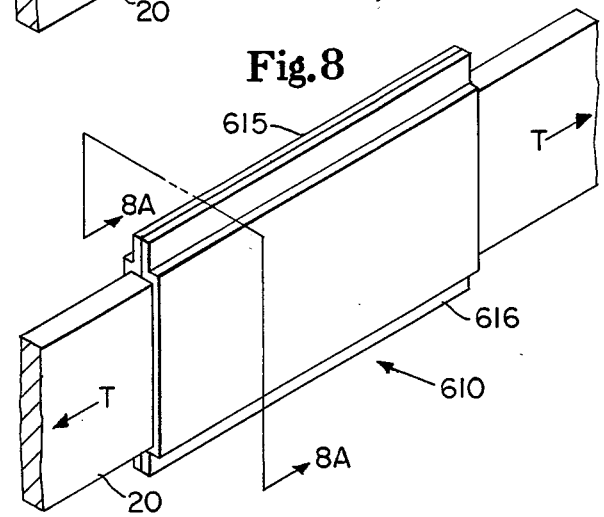

ARTICLE INCLUDING SEGMENT WHICH IS ELASTICALLY SHIRRABLE AFTER MANUFACTURE

This is a continuation-in-part of application Ser. No. 852,053, filed on Apr. 15, 1986, now abandoned.

TECHNICAL FIELD

The present invention relates to an article which includes at least one segment which can be elastically shirred subsequent to its manufacture.

The present invention relates to an article which includes at least one segment which can be elastically shirred by mechanical manipulation of a predetermined portion of the segment.

The present invention has further relation to method and apparatus for applying such a segment to an article while the segment is in a substantially untensioned condition.

The present invention has still further relation to an elastically shirrable segment per se. The segment preferably includes a prestretched and tensioned elastomeric member which is secured in fixed relation to at least one rigidifying member. The composite structure thus formed is strong enough to resist collapse in a direction parallel to the tensile forces acting upon the prestretched and tensioned elastomeric member prior to mechanical manipulation of the composite structure.

The present invention has further relation to method and apparatus for making elastically shirrable segments which include one or more such composite structures.

BACKGROUND OF THE INVENTION

The fit of a garment to the body of the wearer is one of the key aspects of clothing design. Garment fit is critical for several reasons. First, garments that fit well are aesthetically pleasing to the wearer, as well as to others. Second, clothing that fits the body well does not hinder body movement. For instance, clothing that is too tight will prevent the body from undergoing its normal muscular expansions and contractions, causing discomfort to the wearer. Clothing that is too loose can hinder body motion by entangling the body in the garment or by adding unwanted bulk. Third, good fit often provides the function of garment securement. For instance, waist bands hold pants up, hat bands hold hats on, and some cuffs hold sleeves or pant legs in place. Fourth, there is a kind of fit that seals the environment beneath the clothing from leaking to the outer environment, or vice versa. This function is obvious in durable garments such as rainwear or cold weather clothing, and in disposable garments such as disposable diapers.

Elastics of many forms are often used to provide one or more types or garment fit. The forms of these elastics include composite materials such as those used in undergarment waist bands, and homogeneous elastomeric materials such as the waist and legbands found in many disposable diapers. There are also linear, and two-dimensional stretch elastics used in clothing. Waist bands, and elastic cuffs are considered linear, whereas in pantyhose the material stretches in two dimensions to provide a contoured body fit.

A common problem with elastics on factory manufactured articles, such as clothing, is that the amount of tension the elastic applies against the body is not right for each individual wearer. This problem arises because factory made clothing is manufactured in certain discrete sizes. While the elastic tension may be right for a person having dimensions in the middle of a particular size range, the tension may be too light for a slightly smaller person or too great for a somewhat larger person. If the tension is too light the garment may droop, while if too great, the elastics may leave red marks on the skin and cause discomfort.

Achieving garment fit using elastics also poses problems for the manufacturer of garments. First, attaching elastic materials to a garment, especially when the elastic is in a prestretched condition, requires somewhat complex material handling methods. Fixturing is often required to hold the elastic in a stretched condition, or the garment in a shirred or gathered condition while the attachment is made. This extra handling and fixturing can slow down automated production lines. Secondly, once the elastic is attached to the garment and tension is released, the garment shirrs in the area of the elastic making the garment unwieldy as it is passed either on to the next step in the manufacturing process or to a packing operation.

Prior to the development of the materials and method of the present invention, the problems associated with garment elastics have generally been dealt with in two basic ways. In particular, the problem of achieving the right amount of tension for the individual wearer has typically been accomplished by providing multiple fastening locations. These allow the elastic to be stretched different amounts as the garment is fastened to the body. A simple example of this is an elasticized belt for trousers that includes multiple fastening points at the belt buckle. This allows the wearer to select a wide range of waist band tensions. Another example of this is in disposable diapers having an elasticized waist band and tape fasteners. In this instance, the amount of tension in the waist band elastic can be controlled to some degree by the tension the mother applies to the waist band elastic before the tape fasteners are secured. While some degree of tension adjustment is afforded by this method, it is difficult for the person applying the diaper to precisely adjust this tension while the baby is squirming. This method of diaper elastic tensioning also compromises the position of tape attachment from the ideal. For instance, if the elastic is stretched to a great extent to achieve the desired tension, the tape fastening points may be far enough from their ideal location that the overall diaper fit becomes distorted. This distortion may cause poor fit in other critical areas, for example the leg band area.

The problem of assembling garment shirring elastic components which are not in tension when applied has typically been addressed in high speed manufacturing lines by the use of heat shrinkable elastics. These elastics are designed to be attached to a garment such as a disposable diaper while they are in the relaxed state or under low tension. After they are attached, heat is applied to the elastic at some point during or subsequent to the manufacturing process. Upon heating, these elastics contract and regain much of their original elasticity.

These heat shrinkable elastics are manufactured in several forms. Some are homogeneous materials. These are typically thermoplastic elastomers that were stretched to orient their molecular structures after casting. When they are heated after assembly in the diaper, they shrink back, losing some of their orientation. Other heat shrinkable elastics are composite structures such as those disclosed in U.S. Pat. No. 4,552,795 issued to Hansen et al. on Nov. 12, 1985. The structures disclosed by Hansen et al. are preferably comprised of prestretched elastomeric strands that are laminated between two relatively inelastic strips of film with inelastic thermoplastic polymer. Upon the application of heat the thermoplastic polymer softens, allowing the elastic member to move relative to the outer layers, thereby causing the outer layers and the article to which they are secured to elastically contract and shirr. Thus, if this laminate is attached to a portion of a garment, say a diaper waist band, the result upon heating is garment shirring in proportion to the relative movement between the elastic member and the outer layers of the laminate.

While solving many of the problems of elastic material factory assembly, the application of heat required to activate such prestretched and tensioned elastics may, in some circumstances, adversely affect other components in the article to be elasticized. Furthermore, such heat activatable materials do not help in a reasonable way in those situations where elastic adjustment by the consumer is desired. Heat activation by the consumer is impractical because it requires a heat source that is usually unavailable to the consumer, it is potentially dangerous, and it is difficult to reproducibly control without standardized processing conditions and equipment.

Accordingly, it is an object of the present invention to provide both elastic materials and methods of elastic application which avoid the foregoing problems altogether.

It is another object of the present invention to provide a premade elasticized garment including means to enable the person wearing or applying the garment to adjust the elastic tension of the garment to provide just the desired amount of elastic tension.

It is another object of the present invention to provide an elasticized garment including means for the consumer to set or adjust the tension in the garment without having to reposition the fasteners that hold the elastic in its stretched condition.

It is another object of the present invention to provide an article which can be applied to the wearer while it is not in tension and thereafter elasticized.

It is still another object of the present invention to provide method and apparatus for assembling a composite structure including a stretched elastic into an article while the composite structure is in a substantially untensioned condition and thereafter activating the elasticity in the article (either during manufacture or by the consumer) without damaging any of the other components comprising the article.

DISCLOSURE OF THE INVENTION

The elastic materials of the present invention are composite structures. A simple, exemplary embodiment of this composite structure can comprise a three layer laminate. To further describe this structure it is easiest to describe it in terms of a preferred method of manufacture for a specific embodiment.

The first step is to select as a starting material an elastomeric band. While there are many different material and size combinations possible for this band, for purposes of illustration let it be assumed that the band is 0.5 inches wide, 10 inches long, and 0.005 inches thick. This band can be comprised of nearly any elastomeric material, synthetic natural rubber being particularly well suited in situations where long periods of time are likely to pass before the tension in the elastomer is to be released.

The next step is to stretch the band in at least one direction. For example, it can be stretched to 3 times its original length. The band is then preferably clamped at each end to hold it in its outstretched condition. Next, the other two rigidifying layers of the laminate are applied to the stretched band. These other two rigidifying layers may be of identical composition and are preferably comprised of a relatively rigid, brittle material, such as extrusion cast polystyrene. The polystyrene rigidifying layers can be relatively thin, i.e., a thickness of 0.001 inches is sufficient for the exemplary band stretched to 3 times it original length. The rigidifying layers preferably have the same planar dimensions as the outstretched rubber. These polystyrene layers are placed on the top and bottom of the stretched rubber forming a sandwich. These three layers are then heat sealed together under pressure, thereby forming a thermally bonded laminate. After the laminate has cooled, the clamps are removed from the ends of the rubber. Upon clamp removal, the planar laminate structure (exclusive of those portions held in the clamps) remains substantially the same length as the stretched elastic rubber was while it was constrained by the clamps prior to lamination. The resultant laminate is relatively flexible and can easily be handled without maintaining it in tension. The entire laminate band or a segment cut therefrom can be secured to any desired article to be elasticized. For example, the ends of a segment having a length of about five inches could be attached to the opposed portions of an adjustable hat by sewing, riveting etc.

To activate the elastically shirrable segment, as constructed above, one merely has to manually manipulate a portion of the segment with a motion substantial enough to delaminate or crack and delaminate the polystyrene layers and cause relative movement between the prestretched and tensioned elastomeric layer and the rigidifying layers. It will be observed that in the segment which is manipulated, tension is released and the elastomeric layer substantially returns to the length it had prior to the original stretching operation, while the unmanipulated areas remain in a laminate condition and substantially inelastic, i.e., they exhibit substantially the same length they did upon completion of the laminating operation. The tension in the adjustable hat can thus be adjusted by manipulating all or any desired portion of the laminate band.

Laminated, elastically shirrable materials like those described above can be affixed to a garment or other article in any location that requires shirring or tensioning. Once affixed to the garment, the garment can be elastically shirred by manipulating the laminated segment. The amount of shirring produced, and consequently the amount of tension, will be proportional to the length of the segment that is activated by manipulation. Maximum shirring is achieved when the entire length of the laminated segment is involved in a manipulation sufficient to completely delaminate or break and delaminate the regidifying layer or layers from the prestretched elastic layer so as to produce relative movement therebetween. Manipulation of less than the entire length of the laminated segment will cause proportionately less shirring, and consequently less tension in the elasticized article.

It is, of course, recognized that it is not necessary in the practice of the present invention for the entire elastically shirrable segment to comprise a laminate composite structure of the type described earlier herein. For example, the elastically shirrable segment may include one or more such isolated laminate composite structures along its length. Release of tension in any one of the composite structure portions of the segment will shirr that portion of the article to which the ends of the segment are secured, i.e., release of tension in any portion of the segment will draw the ends of the segment closer to one another

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

FIG. 1 is a simplified perspective illustration of an elastically shirrable segment of the present invention shown prior to removal of tension from the stretched elastomeric member;

FIG. 1A is a cross-sectional view of the elastically shirrable segment shown in FIG. 1 taken along section line 1A—1A of FIG. 1;

FIG. 2 is a simplified perspective illustration of an alternative embodiment of an elastically shirrable segment of the present invention;

FIG. 3 is a simplified perspective illustration of another embodiment of an elastically shirrable segment of the present invention;

FIG. 4 is a simplified perspective illustration of an alternative embodiment of an elastically shirrable segment of the present invention;

FIG. 5 is a simplified perspective illustration of an elastically shirrable segment of the type generally shown in FIGS. 1 and 1A after the rigidifying members have been pierced by a sharp instrument to produce stress concentrating features therein;

FIG. 6 is a simplified perspective illustration of an alternative embodiment of an elastically shirrable segment of the present invention wherein the rigidifying members are applied to the tensioned elastomeric member in a fluid state and thereafter dried;

FIG. 7 is a simplified perspective illustration of an alternative elastically shirrable segment of the present invention which is self-activating so as to automatically shirr the article to which it is secured before the article is placed in service;

FIG. 8 is an alternative embodiment of an elastically shirrable segment of the present invention wherein a pair of rigidifying members located on opposite sides of a prestretched elastomeric member are secured to each other, but are not directly secured to the prestretched elastomeric member except at its end points;

FIG. 8B is a simplified perspective illustration of an alternative embodiment of an elastically shirrable segment of the present invention wherein a prestretched elastomeric member is restrained from contracting along its length by preventing the prestretched elastomeric member from expanding in any direction perpendicular to the direction of prestretching;

FIG. 13A is a simplified perspective view, taken from the back sheet side, of another alternative disposable diaper wherein tension in the elastically shirrable segments is released by unfolding the overlapped waistband portions of the diaper to separate the rigidifying members from the tensioned elastomeric members;

DETAILED DESCRIPTION OF THE INVENTION

Figure 8A:
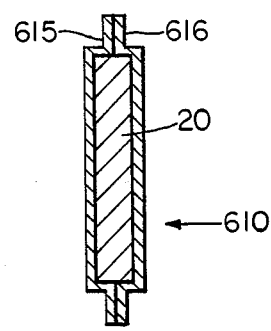
FIG. 8A is a cross-sectional illustration of the elastically shirrable segment shown in FIG. 8 taken along section line 8A—8A of FIG. 8.

Elastically shirrable structures of the present invention may be formed in many different configurations using a variety of materials and methods of manufacture. Exemplary embodiments utilizing differing materials of construction, differing configurations and differing methods of manufacture will be disclosed herein for purposes of illustration only. Various changes and modifications to the exemplary embodiments can be made without departing from the spirit and scope of the invention. Accordingly, these exemplary embodiments are not intended to limit the present invention, as described in the appended claims.

Materials of Construction

Composite elastically shirrable structures of the present invention are typically comprised of up to three material types. These are the elastomeric material, the rigidifying material, and an optional intermediate material such as an adhesive which may be used to attach the elastomeric material to the rigidifying material(s).

These three types of materials are discussed separately hereinafter.

The Elastomeric Material

Preferably, the elastomeric material is a material that can undergo high levels of reversible strain. Elastomers that can be stretched to two or more times their original length and then recover to their original length once the stretching force is removed are particularly useful for the purpose of creating garment shirring. However, elastomers that cannot be reversibly stretched as far may find utility in some applications. Even elastomers which exhibit a degree of irreversible stretch may be utilized, depending upon the particular application.

Elastomers that will maintain a fixed tension when they are stretched and held for long periods of time (perhaps a year) are particularly preferred in situations where long periods of time may pass between the manufacture and use of the elastically shirrable article. Generally these preferred materials are comprised of thermoset rubbers, such as synthetic natural rubbers. Elastomers that will not maintain tension for a long period of time will have more limited utility in practicing the present invention. Their principal use would be in applications where the elastic is to be activated soon after lamination of the composite structure is complete (such as activation on line in a manufacturing plant) or in applications where variable and limited elastic recovery is acceptable. Elastomers that will not maintain tension for extended periods of time are generally comprised of thermoplastics, such as ethylene vinyl acetate copolymer.

The Rigidifying Material

The term "rigid", for the purpose of this invention, is a relative term. It means that the rigidifying material will not foreshorten enough to allow the compressive forces exerted by the stretched elastomer to return the stretched elastomer to its original untensioned length. That is, it is relatively inelastic when compared to the elasticity of the elastomeric component in a given laminate composite structure. Materials such as polystyrene, blends of polystyrene and polyethylene, polyethylene laminated to paper, and surlyn have all been used as a rigidifying component in exemplary elastically shirrable segments of the present invention. These materials all have very different moduli of elasticity from one another, but used appropriately (the right thicknesses, relative material widths, elastic pretension, etc.) they all can work acceptably as a rigidifying member in elastically shirrable segments of the present invention.

The rigidifying member may also be brittle or not. The decision to choose a brittle material over a ductile material depends upon the method of elastic activation desired in the elastically shirrable segment. If it is desirable to activate the elastic by wiggling the composite to cause cracks and delamination in the rigid layer or layers, then a material brittle at the temperature of use is preferred. If however, the elastic is activated by stripping or peeling off the rigid layer from the composite structure, then a more ductile rigidifying material is preferred.

In a yet another embodiment of the present invention, the rigidifying member or layer could be a durable material like steel. For example, it could be a permanent component of a machine that applies the prestretched and tensioned elastic to the garment. In this case, the elastic would be stretched and adhered to a permanent rigid layer such as an endless, flexible steel conveyor band. The resultant laminate comprising the steel conveyor band having the prestretched and tensioned elastomeric member adhered thereto would then be brought into contact with the garment or other article to be elasticized and the elastomeric member would be affixed to the article. Finally, the permanent rigidifying layer would be stripped away leaving the prestretched and tensioned elastomeric member adhered to the article as the article moved downstream. Such a method may be particularly useful for attaching stretched elastic leg bands to a continuously moving web of disposable diapers.

Rigidifying members of the present invention may have many different material configurations. For instance, it could be a flat film, an embossed flat film, a nonwoven fabric, a hollow tube, a rigid foam, a scrim, a laminate of several materials or a molded shape. The materials could have a wide range of thickness, depending upon the tension in the prestretched elastomeric member, and could even be variable in thickness throughout the width and/or length of the composite structure. The rigidifying member or members could also be an integral component of the article to be elasticized rather than an independent element.

The Optional Intermediate Material

The use of an intermediate material to secure the elastomeric member and the rigidifying member to one another is optional in constructing elastically shirrable segments of the present invention. As will also be pointed out in subsequent sections of this specification, it is not always necessary for the rigidifying members to be secured along their length directly to the prestretched elastomeric member. However, in those situations where an intermediate material is employed, it most typically comprises an adhesive. In this capacity, it serves to bond the prestretched and tensioned elastomer to the rigidifying member. This is especially valuable where a natural heat seal bond between the prestretched elastomer and the rigidifying layer is either too strong or too weak. In this case, the adhesive must be selected so as to give the right adhesive forces and so as not to detract from the function of the composite structure.

The optional intermediate material may also comprise more than just an adhesive. It may have considerable bulk relative to the prestretched elastomer and/or rigidifying layer(s). One such example of a composite structure of the present invention could comprise a multiplicity of prestretched elastomeric strands running parallel to a multiplicity of rigidifying strands, both materials enveloped by a matrix comprised of a third material, such as a foam. In this embodiment, the foam must exhibit sufficient adhesive and mechanical strength to hold the composite structure together under the tension of the prestretched elastomeric strands, but be weak enough to collapse with the elastomer when the rigidifying strands are broken. This type of structure may have particular utility as a replacement for durable garment elastics.

In many embodiments of the present invention, an intermediate material is not necessary. However, when the optional intermediate material is not present, it is still a requirement that the prestretched elastomeric member and the rigidifying member be secured in fixed relation to one another so as to form a composite structure which is strong enough to resist collapse in a direction parallel to the tensile forces acting upon the prestretched elastomeric member prior to mechanical manipulation of the composite structure. Methods for securing the prestretched elastomeric member and the rigidifying member directly to one another without use of an intermediate material include heat sealing, solvent bonding (e.g., as by placing a solvent for one or both materials between the layers, and then driving off the solvent), solution casting one layer onto the other, and mechanical interlocking. Bonds made without the optional intermediate layer must also be strong enough to hold the prestretched elastomer in its full, outstretched condition before activation, and weak enough to fail upon whatever form of activation is desired, preferably mechanical manipulation of the composite structure.

In still another embodiment of the present invention, the prestretched elastomeric member and the rigidifying member need not be secured to one another along their length. In simplest terms, this embodiment could comprise a tubular member having a prestretched and tensioned elastomeric member extending through the interior of the tubular member and secured at its opposite ends. In this embodiment, the tubular member must provide sufficient strength to resist the tensile forces acting upon the prestretched elastomeric member until such time as mechanical manipulation of the composite structure destroys the compression resistance of the tubular member and allows relative movement between the prestretched elastomeric member and the tubular member.

In still another embodiment of the present invention, a prestretched elastomeric member could be tightly encapsulated between a pair of polymeric webs which are secured to one another with only its opposing ends secured either directly to the webs or in some other way restrained from retracting into the tunnel formed between the webs, e.g., as by knotting the opposed ends of the stretched elastomeric member. So long as the polymeric webs are secured in intimate relation to the prestretched elastomeric member, the composite structure will resist collapse due to the tensile forces acting upon the prestretched elastomer. However, upon mechanical manipulation of the composite structure, the webs are caused to separate from the prestretched elastomeric member, thereby releasing the tension in the mechanically manipulated portions of the composite structure and shirring the webs in the mechanically manipulated portions of the structure.

In still another embodiment of the present invention, an elastomeric member could be prestretched and thereafter restrained from retracting in the direction of stretching by preventing the elastomeric member from expanding in any direction perpendicular to the direction of prestretching. This is easily understood by thinking of the elastomeric member in terms of its volume, i.e., the product of its length, width, and height dimensions. When the length of an elastomeric material is increased by stretching, its height and/or width is reduced generally in accordance with Poisson's Ratio as it relates to the conservation of volume. By preventing the height and width dimensions of the elongated elastomeric member from expanding, the length of the elastomeric volume will be maintained without any longitudinally aligned forces being applied to prevent it from recovering to its original length. This expanded state will remain stable until such time as the height and/or width dimensions are allowed to expand by removing their respective restraining members. In this embodiment of the present invention, there is no need of a bond between the encapsulating restraint member and the stretched elastomeric member to hold the elastomeric material in its expanded state, since the encapsulating restraint exerts a compressive force on the elastomeric material. This compressive force, which is exerted in a direction perpendicular to the desired direction of shirring, is sufficient to prevent the elastomeric material from expanding in a direction perpendicular to the desired direction of shirring until such time as the elastically shirrable segment is mechanically manipulated or acted upon, i.e., until such time as the encapsulating restraint member is either removed or at least ruptured, so as to release the compressive force. Removal of the compressive force instantaneously restores the tensile force in a direction parallel to the length of the elastomeric member. Accordingly, the elastomeric member retracts in the desired direction of shirring as soon as the encapsulating restraint member is ruptured or removed.

Still another example of an elastically shirrable segment of the present invention comprises an elastomeric member which, when stretched, exhibits a discontinuous or irregular surface. The discontinuous surface could be in the form of openings in a lattice or in the form of indentations, voids, recessed areas, raised areas or an otherwise textured surface. A rigidifying member that extended into these openings, indentations, voids or recessed areas or which was penetrated by raised areas on the elastomeric member while the elastomeric member was in an extended condition can be used to restrain the elastomeric member and prevent it from retracting without the need for adhesive bonding of the rigidifying member to the elastomeric member. Removal of the rigidifying member and release of tension in the affected portion of the tensioned elastomeric member can be accomplished by mechanical manipulation of the composite member or stripping away of the rigidying member to disengage the rigidifying member from the openings, indentations, voids, recessed areas or raised areas in or on the tensioned elastomeric member.

Because there is little or no adhesive bond between the rigidifying member and the stretched elastomeric member, the force needed to cause relative movement between the rigidifying member and the stretched elastomeric member is quite low. Tension in the elastomeric member will be released as soon as the appendages or irregularities on the surface of the rigidifying member which extend into their corresponding relief sites in the expanded elastomeric member are withdrawn or as soon as the raised areas on the expanded elastomeric member are withdrawn from their corresponding relief sites in the rigidifying member. It is of course recognized that the rigidifying member and the stretched elastomeric member may each exhibit both types of irregularities, i.e., raised areas and relief sites. In the latter event, securement of the stretched elastomeric member and the rigidifying member to one another occurs primarily by engagement of complementary raised areas and relief sites with one another. Regardless of the particular configuration, elastically shirrable segments of the aforementioned type are particularly well suited for consumer activation, since they are highly effective in maintaining the elastomeric member in a prestretched and tensioned condition throughout handling and processing operations, yet they require very little force to activate, i.e., they are very strong in shear, but very weak in peel. The peel force can, of course, be adjusted upwardly if desired by providing a degree of bonding in addition to mechanical engagement of the irregular surfaces.

Methods of Manufacturing the Elastically Shirrable Segment

There are a number of processes that can be used to manufacture elastically shirrable segments of the present invention. While not intended to be all inclusive, four general process categories for making elastically shirrable segments of the present invention will be disclosed hereinafter for purposes of illustration. These are: lamination; melt coating; solution casting; and mechanical attachment. Each of these processes can be done in a variety of ways.

Lamination

Lamination of the prestretched elastomer and one or more rigidifying members is a process whereby a previously cast or otherwise processed material is adhered to a second preprocessed material. Adhesion can be achieved by heating one or both materials and holding them together under pressure. Adhesion can also be achieved by placing a solvent for one of the two materials between the materials and holding the materials under pressure until the solvent evaporates. It can also be achieved by adhesive bonding using a third or intermediate material, i.e., the adhesive. This third material is preferably applied as a layer between the materials to be bonded to one another. The adhesive then forms a bond between the two materials. The bond can be deactivated using a number of different forms of mechanical manipulation, including peeling, fracturing, stretching, crushing, etc.

Melt Coating

Composite elastically shirrable segments of the present invention can also be manufactured by flowing the rigidifying layer or layers in a molten state onto the surface of a prestretched elastomer and allowing it to cool before releasing the prestretched elastomer from tension. This could be done using conventional melt coating equipment.

Solution Casting

In this alternative process, the polymer of the rigidifying layers is dissolved in a carrier solvent. The prestretched elastomeric member is then dipped into the carrier solvent. The coating that remains on the prestretched elastomer is then allowed to dry (the solvent evaporates), leaving a rigidifying polymeric coating. The polymeric coating produced by this process has little or no molecular orientation, a particular virtue of the solution casting process.

Mechanical Attachment

The prestretched elastomeric member and the rigidifying member or members can be attached to one another mechanically with no adhesive bond directly between the elastomer member and the rigidifying member or members. An example of this would be a rigid layer molded with tiny sharp spikes on one side that could pierce through the outstretched elastomer and hold it at its prestretched length. Still another example would be a prestretched elastomer with holes along its length with a pair of rigidifying members bonded to one another through the holes in the prestretched elastomeric member.

Possible Uses for the Elastically Shirrable Segments

Elastically shirrable segments of the present invention can be applied to many garments and other articles where gathering or shirring is needed. They can be applied for the purpose of article shirring to both disposable garments and durable garments. In addition, they can be applied to disposable and durable articles where elastic tensioning, particularly user adjustable tensioning, is desired. The following list sets forth illustrative examples of such potential applications:

| | | Advantage |
|---|---|---|
| | 1. Disposable Garment Examples | |
| a. | Disposable Diapers | To provide consumer adjustable waist and leg band tension independent of the position of the garment fasteners (e.g., tapes) |
| b. | Disposable Sanitary Hair Nets or Surgical Caps | To provide the ideal tension for hat securement without causing red marking on the skin |
| c. | Disposable Sanitary Gloves | To provide a means of securement for non-elasticized plastic gloves |
| | 2. Durable Garment Examples | |
| a. | Rental Clothing (snapped or buttoned into the garment for each new user in place of a permanent elactic) | Provides adjustable fit for clothing worn by more than one person (e.g. a tuxedo) |
| b. | As a manufacturer's replacement for garment elastics which must be applied in a stretched condition | Allows the manufacturer to sew or otherwise attach the elastically shirrable segments while they are in a substantially untensioned condition. |
| c. | As a consumer applied replacement for garment elastics which must be attached in a stretched condition | Allows the home tailor to apply the elastically shirrable segments while they are in a substantially untensioned condition. |
| | 3. Non Garment Examples | |
| a. | Trash Bag Closer | Allows the open end of a trash bag to be folded over the trash can without tension, and then to be elasticized and closed prior to disposal. |
| b. | Automobile Seat Covers | Allows easier installation of seat covers by eliminating the need to fight the elastics while hooking the covers in place. |
| c. | Disposable bed sheets | Allows easier installation of corners which are elasticized only after they are properly in place. |

Beyond unidirectional article shirring applications, such as the exemplary applications set forth above, there are still other uses for elastically shirrable segments of the present invention. For instance, elastically shirrable segments of the present invention can also be employed to release elastic forces in more than a single direction, i.e., in two or more directions. Embodiments of the latter type use starting materials similar to those described earlier herein, except that before applying the rigidifying member, the elastomeric member is prestretched in tension in two or more directions instead of one. The result is an elastically shirrable segment that when applied to a garment or other article will draw in or shirr an initially planar portion of the article in two or more directions rather than in just one direction, as in the unidirectional examples described earlier herein.

Preferred Ways of Incorporating Elastically Shirrable Segments into An Article While not intended to be an exhustive listing, the following are illustrative of ways to attach elastically shirrable segments of the present invention to a garment or other article:

1. Heat Bonding
    a. With or without an adhesive
    b. Discrete bonds, or continuous bonding along the length of the composite structure 2. Ultrasonic Bonding
    a. With or without additional heat
    b. With or without adhesive
    c. In discrete or intermittent patterns 3. Mechanical Attachment
    (e.g. within a tubular portion of the garment with the elastic knotted at the ends, by sewing, with staples, etc.)

4. Using Adhesive
    (e.g., hot melt, cold set, pressure sensitive, and contact adhesives)

In selecting a particular means of attachment to the garment or other article, it is in most cases preferable to attach the garment or article to be elastically shirred securely to the prestretched elastomeric component in the composite structure rather than to the rigidifying layer. This is generally so because in order for the composite to release tension in the prestretched elastomeric member, relative movement must occur between the prestretched elastomeric member and the rigidifying member. In the most extreme case, the rigidifying member is completely stripped away. Therefore, in many applications it is highly desirable to have the prestretched elastomeric member exposed in some portions of the composite for the purpose of providing points or areas for attachment to the garment or other article to be elastically shirred.

Preferred Ways of Releasing the Tension in the Prestretched and Tensioned Elastomeric Member There are various ways to release tension in the prestretched elastomeric member in composite structures of the present invention. While the following list is not intended to be exhaustive, it does set forth, for illustrative purposes, a wide variety of possible tension release methods:

1. Mechanical Manipulation by Hand
    a. Stretch the entire composite structure comprising the prestretched elastomeric member and the rigidifying member(s).
    b. Stretch a discrete length of the composite structure.
    c. Scrub, twist or wiggle a portion of the composite structure between the fingers.
    d. Squeeze or crush the composite structure (especially a composite structure having a three-dimensional cross-section) between the fingers.
    e. Stretch the composite structure in a direction perpendicular to the tensile forces applied by the prestretched elastomer.
    f. Strip off the rigidifying member along the length or across the width of the composite structure.
        i. Strip off entire layers.
        ii. Strip off a portion of the layer.
    g. Unfold a portion of the article to which both the exposed surface of the elastomeric member and the exposed surface of the rigidifying member have been secured.

In such an embodiment of the present invention means are preferably provided to release the restrained elastomeric member without removing the rigidifying member from the finished product. This may be accomplished by incorporating the rigidifying member as a permanent part of the finished product, e.g., the exposed elastomeric surface of a strippable release type elastically shirrable segment of the present invention can be permanently bonded to the product to be elasticized and thereafter folded over onto the product, such that the exposed surface of the rigidifying member also contacts and is bonded to the surface of the product to be elasticized. The resultant product can be elasticized by simply unfolding the product to its original position, thereby separating the rigidifying member and the elastomeric member from one another along their respective lengths. This allows the prestretched elastomeric member to recover to its original dimension, thereby elastically shirring the article in the area of attachment, while the rigidifying member remains adhered to the surface of the product.

2. Mechanical Manipulation by Machine
    a. All of the above manual methods could be automated.
    b. Delaminate the composite structure by vibrations such as ultrasound.
    c. Pass the composite structure through knurled rolls.
    d. Activate a portion, but not all of the elastic length by mechanical manipulation of only a portion of the composite structure, leaving the end user or consumer some portion of the composite structure to activate manually.

3. Mechanical Manipulation Using a Bond Breaking Element

A bond breaking element such as a string, filament, button, etc. could be added to the composite structure for the purpose of disrupting the bond between the prestretched elastomeric member and the rigidifying member or members. For instance, one or more bond breaking filaments could be sealed between the elastomeric member and the rigidifying member or members. Upon ripping up the filament, the bond between the prestretched elastomeric member and the rigidifying member or members could be broken, thereby permitting relative movement therebetween and a resultant release of tension.

4. Self Activating Prior to End Use

In yet another embodiment of the present invention, the release of tension in the prestretched elastomeric member is accomplished without mechanical manipulation of the composite structure. For elastically shirrable segments intended to simplify the manufacture of elasticized garments, the materials of construction are carefully selected so that over some predetermined period of time the rigidifying layer and/or the adhesive layer used to initially secure the prestretched elastomeric member in an extended condition creeps. Elastically shirrable segments of the aforementioned type could be applied to an article in a substantially untensioned condition, but the article would arrive in the end user's hands in an elastically shirred condition.

EXEMPLARY EMBODIMENTS

As pointed out earlier herein, numerous benefits afforded by practicing the present invention can be obtained in a variety of ways. The following exemplary embodiments of the present invention are merely representative:

EXAMPLE I

Solid Seal Configuration

The embodiment illustrated in the simplified perspective of FIG. 1 comprises thin layers of film 15,16 continuously sealed on each side of a stretched rubber 20 while it is subject to tension "T", thereby forming a tri-laminate composite structure 10 of the present invention.

The rubber is maintained in tension "T" during the fabrication process by stretching between a pair of fixed pins 25,30, wrapping the ends of the prestretched rubber about the opposed pins and thereafter securing each end by means of opposing clamping forces "F", as generally shown in FIG. 1.

Materials

Rubber (20)-Fulflex 9411-1" wide×0.007" thick (IN2732) as available from Fulflex, Inc. Bristol, R.I.

Film (15,16) - Dow Chemical Trycite T-100 D having a thickness of 0.0015", as available from Dow Chemical, Midland Michigan

Equipment

Vertrod-Thermal Impulse Heat Sealer Model 30P/PRS 1500 Watt, as available from Vertrod Corp., Brooklyn, N.Y.

Heat Setting—3; Dwell Setting—Max (10) Clamping fixture—A 36" piece of angle steel with 3" long ½ bolts secured near each end (shown as pins 25 and 30 in FIG. 1)

Procedure

The rubber 20 was stretched to twice its original untensioned length and clamped into the clamping fixture using 2" electrical alligator clips at each end (opposing forces "F" in FIG. 1). The rubber 20 was then cleaned by directing compressed air at the clamped rubber to remove dirt or unwanted powder. One inch wide strips of Trycite film were placed on both sides of the stretched and clamped rubber 20. While the rubber 20 was held in tension "T" produced by its extension in the clamping fixture, this 3-layer sandwich was placed into the sealing position on the Vertrod Impulse Heat Sealer. Several (5-8) seals (each ⅛"-3/16" wide and approximately 30" long) were made until the entire surface between the stretched rubber 20 and the rigidifying film layers appeared to be sealed. The clamping fixture was then removed from the Vertrod and the sealed trilaminate composite structure 10 was carefully unclamped.

In this particular laminate composite construction, which is shown in greatly enlarged form in the cross-section of FIG. 1A, the restraint forces on both sides of the extended elastomeric member 20 are substantially equal. This type of construction is particularly good for continuous manufacturing operations, since the laminate composite 10 is substantially planar and stable; it has the appearance of a smooth, flat non-elastic laminate film; it exhibits substantially no elastic properties in spite of the presence of tension "T" in the prestretched elastomeric member 20; and it will remain in this state until it is activated by using one or more of the mechanical manipulation methods described earlier herein.

When tension is released in the prestretched elastomeric member 20 by mechanical manipulation of the composite 10, the film layers 15,16 delaminate from the prestretched rubber 20, permitting relative movement therebetween. The composite structure 10 can be activated in small portions or along its entire length, depending upon the location and degree of mechanical manipulation.

The amount of elastic recovery obtained using laminate structures of the type generally shown in FIGS. 1 and 1A will, of course, depend upon the initial degree of extension of the elastomeric member as well as the strength of the rigidifying member or members. By proper selection of materials and tension, elastic recovery rates of over 400 percent have been obtained using configurations similar to the one shown in FIGS. 1 and 1A.

EXAMPLE II

Intermittent Seal Configuration

There are many ways in which non-continuously sealed embodiments of the present invention can be made. The embodiments described in connection with Example II provided a simple way to demonstrate the basic concept.

Materials: (same as Example I)
Equipment: (same as Example I)

Procedure

Construction of the first Example II embodiment was the same as for the Example I embodiment up to the point of heat sealing in the Vertrod Impulse Heat Sealer. The Vertrod was set on Heat-4 and Dwell-Max (10). However, in the Example II embodiment a centrally located section (about ⅓ the width of the stretched rubber 20) extending along the length of the stretched rubber was not heat sealed to the rigidifying members 15,16. Only seals along the longitudinal edges of the prestretched rubber 20 were made.

For most purposes, composite structures of the type described above behaved similarly to the structures described in connection with Example I. However, in the Example II embodiments, the non-sealed sections of prestretched rubber 20 will not be exposed to the higher temperatures needed for sealing, thereby reducing the amount of thermal degradation that might otherwise take place in the prestretched elastomeric member in that area. If the unsealed areas are also left uncovered by the rigidifying members, the exposed areas provide ideal sites to attach the composite material to an article or garment. In this regard, see embodiment 110 shown in FIG. 2, wherein the stretched rubber 20 is restrained by two pairs of rigidifying members 115,116.

As shown in FIG. 3, it is also possible to seal the prestretched elastomeric member 20 to rigidifying members 215,216 at isolated locations 217,219, respectively, along the length of the prestretched elastomeric member while the elastomeric member is subject to tension "T". If an elastically shirrable segment containing the resulting composite structure 210 is applied to an article or garment while it is still maintained in tension "T", it will produce a structure which is partially elasticized upon release of the tension from the ends of the segment. However the partially elasticized article can be further elasticized, i.e., the tension can be increased, by mechanically manipulating the sealed portions 217,219 of the composite 210 to release the tension remaining in the sealed isolated portions of the composite.

EXAMPLE III

Rigidifying Member on One Side Only

A two layer embodiment of the present invention (rubber and film on one side only) can be made with proper selection of film thickness and degree of tension "T" in the elastomeric member.

Materials:
Rubber (same as Examples I and II)
Film (The same type of film as was used in Examples I and II, but its thickness ranged from 0.0015" to over 0.005" on successive samples.

Equipment:
Vertrod (same as Example I)
Clamping fixture (same as Example I)
Procedure:

The same basic procedure described in connection with Example I was employed for constructing the elastically shirrable segments of Example III, except that the prestretched and tensioned rubber 20 had a layer of rigidifying film 315 heat sealed to only one side thereof to form a two-layer composite 310, as generally shown in FIG. 4. From the series of samples made, it was observed that if the rigidifying film 315 had a thickness in the range of one to two mils (0.001"-0.002"), the composite sample 310 tended to curl up in a roll when unclamped. However then the rigidifying film exhibited a thickness in the range of four to five mils (0.004"-0.005"), the composite structure 310 tended to remain planar when unclamped.

Using a one-sided construction of the type described in connection with Example III allows partial or continuous sealing of an article or garment to be elasticized to the exposed side of the prestretched and tensioned elastomeric member 20. Such complete accessibility makes it relatively easy to affix the composite structure 30 while in a substantially untensioned condition to the article or garment to be elasticized in nearly any desired location using nearly any type of securement means and/or any type of securement pattern.

EXAMPLE IV

Solid Seal Configuration with Stress Concentrating Features in Rigidifying Members In certain instances it may be desirable that very little mechanical manipulation of the laminate composite structure be required to release the tension in the prestretched elastomeric member. A process that can be performed on composite structures of the present invention, such as those described in connection with Example I, is mechanical perforation of the rigidifying film layers 15 and 16 to reduce the manipulation needed to cause the prestretched elastomeric member 20 to regain its elasticity.

Materials:
Solid seal configuration composite structure as described in Example I and generally shown in FIGS. 1 and 1A.

Equipment:

A sharp pointed tool—awl, scribe, etc.
A soft solid rubber at least ⅛" thick (silicone, natural rubber, or etc.)

Procedure:

Small fracture areas or holes 28 can be created in rigidifying members 15 and 16 by placing the flat sealed composite structure 10 on the soft rubber and poking small holes in it with sharp object, as generally shown in FIG. 5. The more holes 28, the more dramatic the reduction in mechanical manipulation required to release tension in the prestretched elastomeric member 20 in the resultant composite structure 10'. Making 1/16" diameter holes 28 on ⅛ centers worked particularly well.

Such post-treatment operations can, if desired, be performed as an integral part of the construction procedure for elastically shirrable segments requiring mechanical manipulation to release tension in the stretched elastomeric member. The object of such post-treating is to weaken the rigidifying member of members and/or to control where the rigidifying member or members fracture during mechanical manipulation of the composite structure. Such post-treatment processes can also be employed to cause specific areas of the prestretched elastomeric member to be released first or to be released with less effort than other areas of the elastically shirrable segment. The actual breakup or fraction pattern in the rigidifying member or members can be controlled by the design and/or location of the holes 28 (or other stress concentrating features) created by the post-treatment process.

EXAMPLE V

Fluid Coating of a Prestretched and Tensioned Elastomeric Member

The elastically shirrable segments of Example V each comprised a prestretched elastomeric member 20 held in a fixed position in a clamp system and then coated with thin coats 415,416 of a fluid rigidifying material.

Materials:
Rubber—Fulflex 9411-⅜" wide×0.007" thick, as available from Fulflex Inc. of Bristol, R.I.
Rigidifying Layer—Polystyrene, Grade IR2PO, as available from Amoco Chemicals Corp., Naperville, Ill; Solvent, Dichloromethane, as available from MCB Manufacturing Chemists, Inc., Cincinnati, Ohio; and filler, Transword Correction Fluid (Stock No. TW564), as available from Elberon Products, Cincinnati, Ohio.

Equipment Used:
Clamping fixture—generally similar to the clamping fixture used in connection with Example 1

Procedure:
The rigidifying layer was mixed by dissolving 50 gms of a polystyrene resin with 50 ml of dichloromethane. To this mix one bottle of white-out correction fluid with fibers and solvent base (approximately 22 gms.) were added.

The ⅜" wide rubber was then stretched to at least twice its untensioned length and secured in the clamping fixture under tension "T". An even coating of the fluid mixture described above was painted on both sides of the prestretched rubber with a brush, and the solvent was flashed off, leaving behind rigid coatings 415,416 of styrene filled with fibers on the opposed surfaces of the prestretched rubber 20. A coating thickness of approximately one mil (0.001") proved sufficient to prevent collapse of the prestretched and tensioned elastomeric member 20 prior to mechanical manipulation of the resultant composite structure 410 shown generally in FIG. 6.

EXAMPLE VI

Prestretched Elastomeric Member Having Peelable Rigidifying Member

Elastically shirrable segments of the present invention can also be fabricated so that release of tension from the prestretched elastomeric member is effected by peeling away the rigidifying member. The elastically shirrable segments of Example VI are of this variety.

Materials:

Rubber—Fulflex 9411-$\frac{1}{2}$″ wide×0.007″ thick (IN2732), as available from Fulflex Inc., Bristol, R.I.

Film—4 mil thick polyethylene, as available from Ohio Poly Corp., Carrolton, Ohio Adhesive—3M Medical Transfer Adhesive Tape (1524), as available from 3M Industrial Products Division, St. Paul, Minn.

Equipment:

Vertrod—Thermal Impulse Heat Sealer Model 24PCS-$\frac{1}{4}$, as available from Vertrod Corp., Brooklyn, N.Y.

Procedure:

The rubber elastomeric member was cut to length (about 7″), rubbed with a piece of cloth to remove any foreign matter from its surfaces, extended to approximately 2.5 times its original untensioned length and taped at each end onto the Vertrod heating surface with masking tape. The polyethylene film comprising the rigidifying member was cut into pieces measuring approximately 1.5 inches×10 inches. One piece of the polyethylene film was placed between the Vertrod heating surface and the extended elastomer with its larger dimensin aligned with the larger dimension of the stretched elastomer. The Vertrod heating control was set to 5, the dwell to 10 (max) and the materials were heat sealed to one another. The partially sealed materials were then moved and sealed again in the area that was not sealed originally. This procedure was repeated until the resulting laminate exhibited a one-sided solid seal configuration generally similar to that described in connection with Example III and illustrated in FIG. 4.

The laminate was then removed, the Vertrod heat setting adjusted to 10 (max.) and one end of the laminate was placed into the Vertrod jaws so that the major dimension of the laminate was perpendicular to the major dimension of the sealing area of the jaws. The last $\frac{1}{4}$″ of the laminate was then sealed again to provide maximum seal strength and thereby minimize spontaneous delamination at that end. The laminate was then removed from the Vertrod and its opposite end was grasped firmly between the thumb and forefinger at a point about $\frac{3}{4}$″ from the end of the segment. The protruding elastic was grasped and pulled until delamination of the last $\frac{3}{4}$″ of the laminate occurred. Without changing Vertrod settings, the delaminated end of the structure was placed into the Vertrod so that its length was oriented perpendicular to the jaws of the Vertrod and thereafter sealed to within the last $\frac{3}{8}$″ of the laminate. This left an unsecured tab of polyethylene approximately $\frac{3}{8}$″ in length to grasp for later release of tension in the prestretched elastomer. At this time there was also an excess of untensioned rubber remaining at each end of the laminate structure.

To prevent coiling of the laminate it was placed on a solid surface with the elastomer side up. Each end of the elastomer was placed under a little tension and taped. The excess polyethylene was then trimmed to approximately equal the width of the elastomer. With the laminate still taped, an adhesive was applied to the exposed prestretched elastomeric member along the length of the laminate structure, and a disposable diaper backsheet blank comprised of polyethylene film was attached to the exposed elastomeric member at the back waist location by means of the adhesive. After attachment of the backsheet blank the protruding ends of untensioned rubber that were not attached to the backsheet were trimmed. This procedure was repeated for the front waist location using another identical laminate sample.

A disposable diaper using the aforementioned back sheet was then secured about the waist of a baby model by suitable fasteners, such as adhesive tapes, and the waist band tension was thereafter adjusted by stripping the polyethylene rigidifying member from the front and back waist band portions of the diaper. The greater the amount of rigidifying material removed, the greater was the tension in the diaper waist band.

EXAMPLE VI A

Prestretched Elastomeric Member Having Rigidifying Member Secured Thereto Without Adhesive Example VI A is somewhat similar to Example VI in its method of activation, but construction of the Example VI A embodiment is simplified in that it does not rely upon an adhesive bond between the rigidifying member and elastomeric member.

Materials:

Rubber—#4141 Soft-Stretch Elastic, as available from Risdon, Spartanburg, SC.

Film—#6763 Pet-G[glycol modified (Poly)ethylene terephthalate], as available from Eastman Chemical Products, Kingsport, TN.

Equipment:

Vertrod—Thermal Impulse Sealer Model 24″ LAB-SP, as available from Vertrod Corporation, Brooklyn, NY.

Procedure:

The rubber was stretched to twice its original untensioned length and clamped into the clamping fixture in the manner generally described in connection with the Example I embodiment. A strip of Pet-G film measuring approximately $\frac{5}{8}$″ wide×12″ ong was placed on the bottom sealer jaw of the Vertrod sealer. The stretched, clamped rubber was superposed on the film. The Vertrod sealer, which was equipped with a water cooled heater bar having a width of approximately $\frac{3}{4}$″, was applied to the composite at a gauge pressure of approximately 30 pounds per square inch for a period of about 3.5 seconds at a heater current of about 80 amps.

In the embodiment of the Example VI A, the Pet-G film was only heated to a temperature which allows partial flow of the film into the void spaces existing between the fibers that make up the Soft-Stretch Elastic material. Evidence that the primary securement mechanism involved in this execution is one of mechanical engagement of the Pet-G film in the void spaces of the Soft-Stretch Elastic material could be observed by examining the rigidifying member after activation of the resultant elastically shirrable segment by removal of the rigidifying member. Careful examination of the surface of the rigidifying member disclosed an embossed pattern which was nearly an exact reciprocal of the surface of the stretched Soft-Stretch Elastic material. However, there was no evidence of appreciable fusion bonding of the two materials to one another after separation had been effected, i.e., there were no individual fibers adhering to the rigidifying member after its separation from the tensioned Soft-Stretch Elastic material.

EXAMPLE VII

Solid Seal Configuration Which is Self-Activating Prior to End Use

In certain instances it may be desirable that the release of tension in the prestretched elastomeric member of composite structures of the present invention automatically occur without mechanical manipulation of the composite structure. Materials of the latter type are referred to as self-activating, i.e., the elastic composite could be applied to an article while in a substantially untensioned condition, but arrive in the end user's hands in an elastically shirred condition due to the self-activation which takes place after attachment of the elastically shirrable segment to the article or garment in question.

The composite structure embodiment which is illustrated in simplified perspective in FIG. 7 comprises a layer of masking tape 515,516 continuously secured to each side of a stretched rubber 20 while it is subject to tension "T", thereby forming a trilaminate composite structure 510 of the present invention.

Materials:
Rubber (20)—Fulflex 9411, ¼" wide by 0.007" thick, as available from Fulflex Inc., Bristol, R.I. Rigidifying Members (515,516)—Spectape ® pressure sensitive masking tape, as available from Spectape, Inc., Erlanger, Ky.

Procedure:
A 6" long piece of rubber 20 was extended to 3 times its original untensioned length and a layer of the pressure sensitive masking tape 515, 516 was adhered to each side of the prestretched rubber by means of the pressure sensitive adhesive 518 on the tape, as generally shown in FIG. 7. The trilaminate structure 510 thus formed was pressed together by hand. The overlapping edges of the tape were trimmed so as to equal the width of the stretched rubber 20 and cut to the same overall length as the stretched rubber. The resultant laminate composite structure 510 maintained the stretched rubber in its fully extended condition for only a short time when tension "T" on the segment was released. It was observed that the stretched rubber 20 began to slowly contract. After about an hour had passed, the tapes 515, 516 had shirred along substantially all of their length, and the rubber 20 had returned to its original untensioned length.

Laminate composite structures of this type find particular utility where it is desired to apply the composite to an article or garment while in a substantially untensioned condition, yet provide the end user with an elastically shirred article which is ready for immediate use.

EXAMPLE VIII

Rigidifying Members Secured to Each Other But Not To Prestretched Elastomeric Member The three layer laminate composite structure of Example VIII can be made by securing a pair of rigidifying members to one another, but not to the prestretched elastomeric member. The ends of the prestretched elastomeric member can be secured either to the ends of the rigidifying members or otherwise prevented from retracting within the tunnel formed by the rigidifying members, as by tying knots at the ends of the stretched elastomer.

Materials:
Rubber (20)—Fulflex 9411-3/16" wide by 0.004" thick by 6" long, as available from Fulflex, Inc., Bristol, R.I.
Rigidifying Members (615, 616)—3 mil thick polystyrene 1" wide by 8" long, extrusion cast from Amoco IR2PO polystyrene, as available from Amoco Chemicals Corp., Naperville, Ill.

Procedure:
The rubber 20 was stretched to three times its original untensioned length. A layer 615, 616 of 3 mil polystyrene 1" wide by 8" long was placed adjacent each surface of the prestretched rubber. The two layers of polystyrene were heat sealed to one another in the ¼" wide areas adjacent the edges of the stretched rubber such that no sealing occurred between the polystyrene layers and the stretched rubber along most of the length of the composite, 610. After the stretched rubber 20 was encased between the polystyrene sheets, as generally shown in FIGS. 8 and 8A, the prestretched rubber 20 was heat sealed to the encapsulating polystyrene sheets 615, 616 at each end thereof to prevent retraction of the prestretched rubber into the tunnel formed between the sealed sheets. The polystyrene rigidifying members 615, 616 were then trimmed to within a ¼" of the edges of the stretched rubber 20 and the untensioned rubber segments extending beyond the ends of the polystyrene sheets were trimmed so that 1" of untensioned rubber was present on each end of the resultant laminate composite structure 610.

Tension in the prestretched rubber contained within the casing formed by the polystyrene sheets is released by mechanically manipulating the composite structure 610 intermediate those points where it is sealed to the ends of the polystyrene rigidifying members 615, 616.

EXAMPLE VIII A

Controlled Volume Restraint Configuration

In the Example VIII A embodiment 818 shown in FIG. 8B, which is based upon a controlled volume restraint system, no heat or adhesive is required to either make or activate the elastically shirrable segment.

Materials:
Latex Laboratory Tubing #203-166, as available from Curtin Matheson Scientific, Houston, TX.
Heavy Duty Aluminum Foil, as available from Reynolds Wrap, Richmond, VA.
Spectape ®, as available from Spectape of the Midwest, Cincinnati, Ohio.
String-Dental Floss as available from Johnson and Johnson Dental Products, East Windor, NJ.

Procedure:
A section of latex rubber tubing (element 21 in FIG. 8B) was longitudinally stretched to approximately 400% of its relaxed length and clamped into a holding fixture, as generally described in connection with the embodiment of Example I. This extended tube was snugly wrapped with heavy duty aluminum foil (element 816 in FIG. 8B). Each end of the foil was wrapped with a layer of tape (elements 737 in FIG. 8B) perpendicular to the axis of the stretched tubing, and another length of tape (element 738 in FIG. 8B) was placed over the entire length of the foil in a direction parallel to the axis of the tubing to form an encapsulating restraint member. A filament comprising a piece of dental floss string (element 909 in FIG. 8B) was placed outside the tube and under the aluminum foil prior to wrapping, to facilitate activation of the resultant elastically shirrable segment.

The Example VIII A embodiment 818 was removed from the clamping fixture and the latex tubing was allowed to recover in those areas which were not covered by the aluminum foil restraint member. (These end points would normally be attached to the article to be elastically shirred.) However, the portion of the tubing which was snugly wrapped by the aluminum foil encapsulating restraint member while the elastomeric member was in a prestretched condition remained in an extended condition so long as the tube was constrained from expansion in a direction perpendicular to the axis of the tube by the aluminum foil encapsulating restraint member, i.e., the longitudinally extended elastomeric member was maintained in a state of compression perpendicular to the desired direction of shirring by the encapsulating restraint member. Recovery or activation of the longitudinally extended section of the tubing was accomplished by pulling the filament or string 909, which ruptured the foil/tape structure comprising the encapsulating restraint member covering the stretched tubing. This allowed the restrained portion of the tubing to expand in cross-section, i.e., radially, as well as retract to its original length.

The Example VIII A embodiment 818 clearly demonstrated that it is feasible to maintain a prestretched elastomeric member in a longitudinally extended condition by employing an encapsulating restraint member which restricts its volumetric expansion in any direction perpendicular to the direction of prestretching without the need for any type of seal or bond directly between the elastomeric member and the encapsulating restraint member.

EXAMPLE IX

Disposable Diaper Including an Elastically Shirrable Segment

Figure 9:
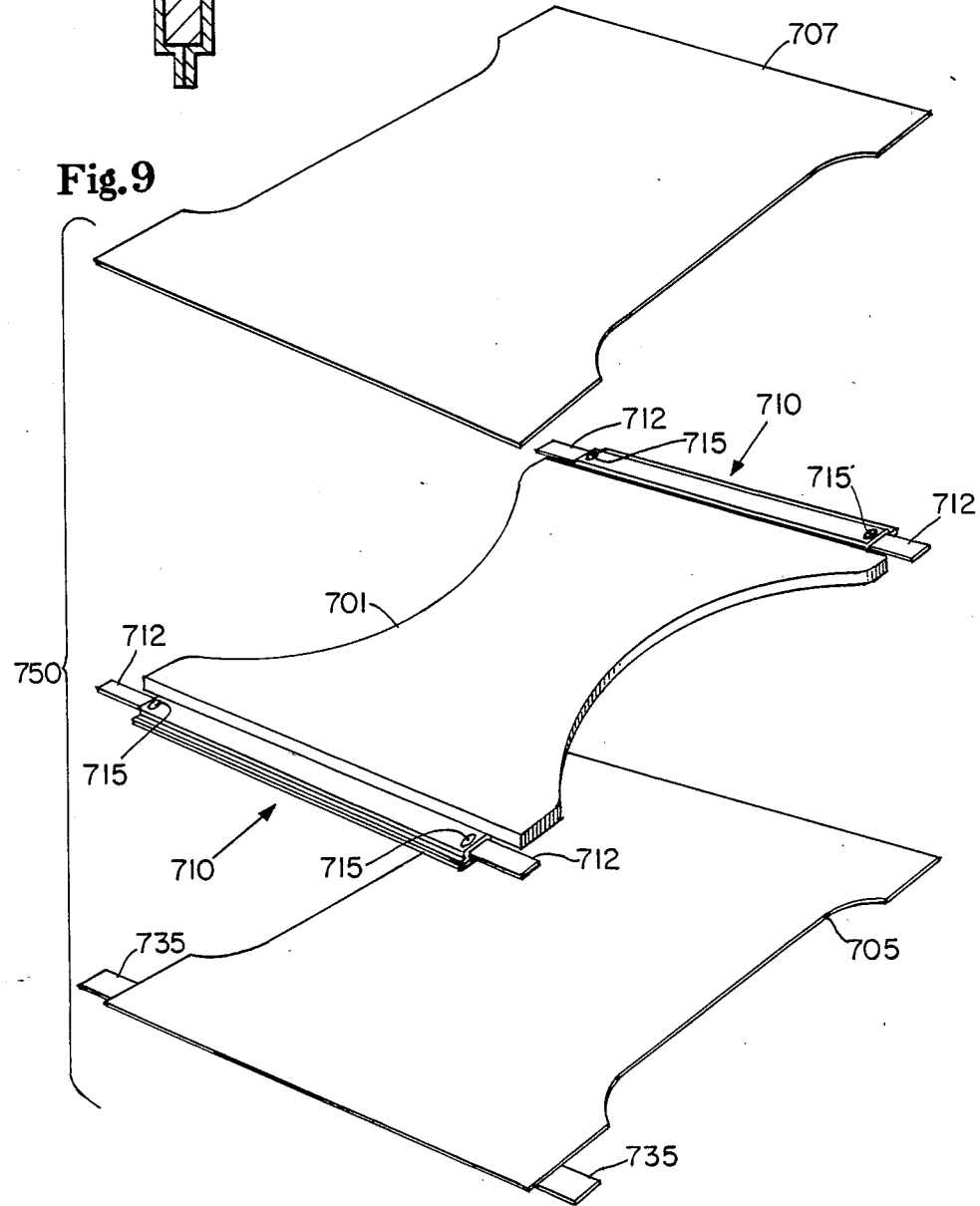
FIG. 9 is an exploded view of a disposable diaper including an elastically shirrable segment of the present invention at each of its opposed waist band areas.

The following procedur, which is schematically represented in the exploded view of FIG. 9, was used to construct a disposable diaper 750 that demonstrated the feasibility of a user activated elastic waist band:

An hourglass shaped disposable diaper core 701 similar to those used in Luvs ® disposable diapers manufactured by The Proctor & Gamble Company, Cincinnati, Ohio, was placed on a backsheet 705 measuring approximately 12"×20" and comprised of 0.0013" thick polyethylene. The core was held in place by strips of double-sided adhesive tape (not shown), such as 1524 Medical Transfer Adhesive tape available from 3M Industrial Products Division, Minneapolis, Minn. The double-sided adhesive tape (not shown) was also placed on the backsheet 705 approximately ½" outside the perimeter of the diaper core 701 and in the area of the diaper waist band.

A 10" long elastically shirrable segment 710 similar to that described in connection with Example VIII and having untensioned elastic ears 712 on both its ends was attached to the backsheet 705, as shown in FIG. 9, near each of the waist band portions of the diaper. Note that tension was maintained in the encapsulated portions of the elastomeric member in each segment 710 by a pair of heat seals 715 located at the opposite ends of the rigidifying members. Each elastically shirrable segment 710 was fastened to the innermost face of the backsheet 705 by double-sided tape only at its untensioned ends 712, where the elastic was exposed. A non-woven topsheet 707 comprised of approximately 0.005" thick polypropylene, as available from Scott Paper Company, Philadelphia, PA., was secured to the exposed innermost portions of the diaper back sheet 705 using the previously laid medical transfer adhesive tape (not shown) to produce an hourglass-shaped disposable baby diaper 750.

Figure 10:
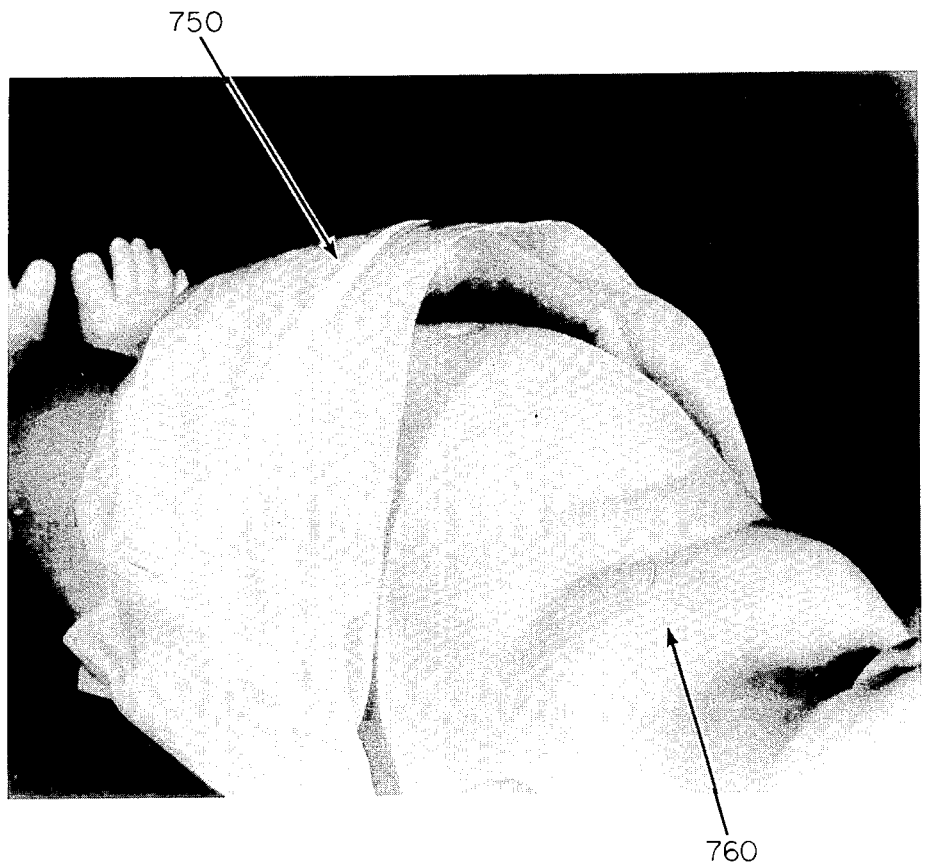
FIG. 10 is a photograph of an assembled diaper of the type generally illustrated in FIG. 9 applied about the torso of a baby model, said diaper being shown prior to the release of tension in either of the elastically shirrable segments contained therein.
Figure 11:
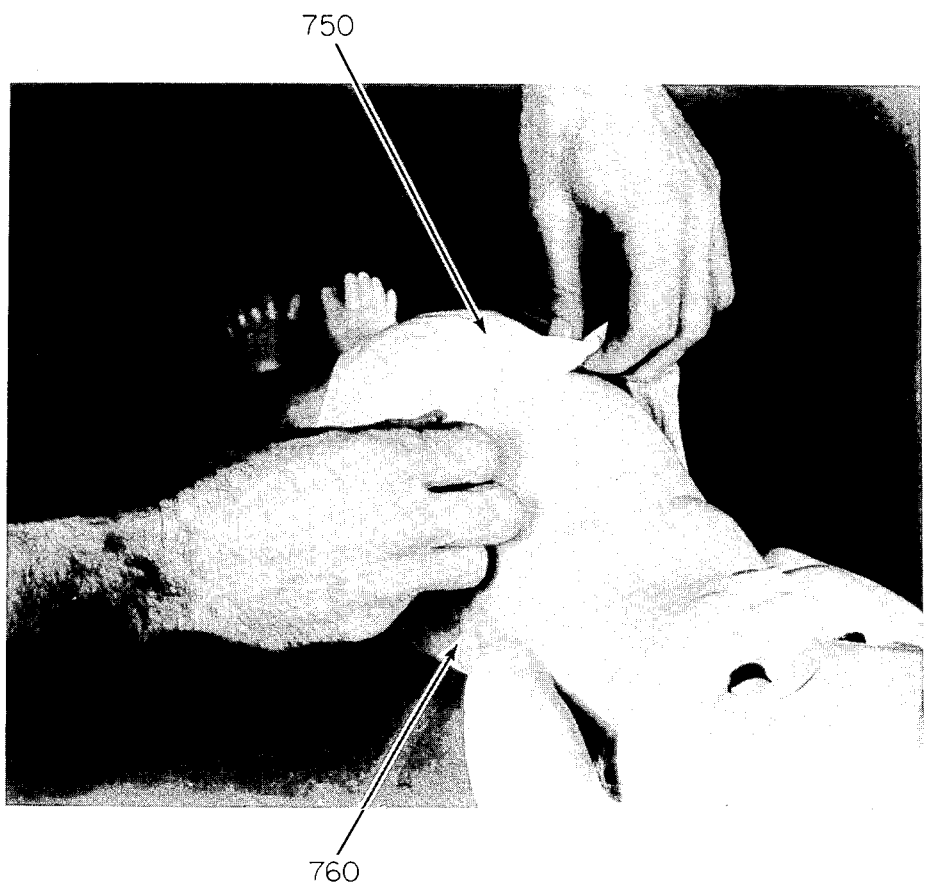
FIG. 11 is a photograph of the diaper shown in FIG. 10 demonstrating mechanical manipulation of one of the elastically shirrable segments contained in a waist band portion of the diaper to release tension in the prestretched elastomeric member.
Figure 12:
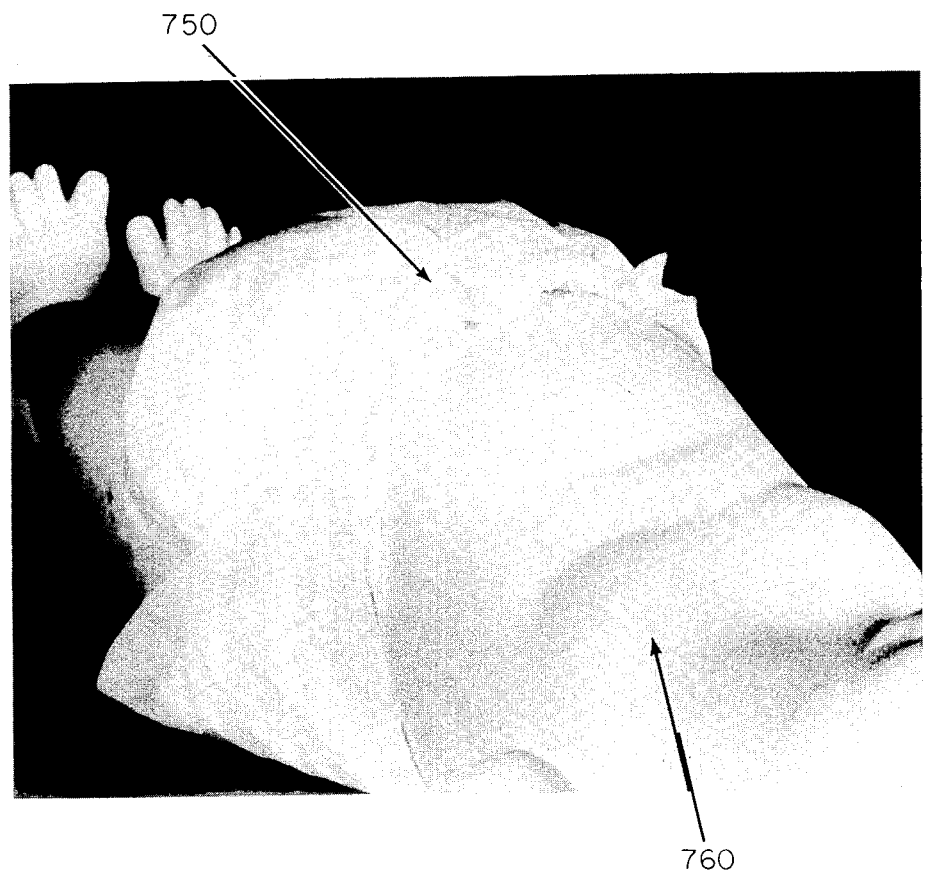
FIG. 12 is a photograph of the diaper shown in FIGS. 10 and 11 after the elastically shirrable segments have been mechanically manipulated along their entire length.

Testing:

The disposable baby diaper 750 was put on a baby model 760 using pressure sensitive adhesive tape tabs 735 to hold the diaper on the baby model as it would be in actual use. The disposable diaper 750 is shown in place, but prior to the release of tension in the prestretched elastomeric members included in either of the elastically shirrable segments 710 in the photograph of FIG. 10. Note the lack of tension about the baby model's waist. Manual manipulation, as shown in FIG. 11, was thereafter used to release the tension in both of the elastically shirrable segments 710 located in the diaper waist band. The amount of elasticity desired to obtain good diaper fit was easily controlled by the degree and location of mechanical manipulation. This demonstrated that user manipulation of an article containing an elastically shirrable segment of the present invention causes the article, in this case the diaper waist band, to become elastically shirred, as generally shown in FIG. 12.

EXAMPLE X

Disposable Diaper Having Peelable Rigidifying Member

The disposable baby diaper of Example X was made utilizing construction techniques generally similar to those outlined in connection with the diaper of Example IX. However, the elastically shirrable segments 710 located intermediate the topsheet 707 and the backsheet 705 in the diaper embodiment 750 were eliminated in the diaper embodiment 850 shown generally in FIG. 13. In place of the elastically shirrable segments 710, a pair of elastically shirrable segments 810 were secured to the outermost surface of the backsheet 705, again utilizing double-sided adhesive tape. The elastically shirrable segments 810 were constructed generally in accordance with the description set forth in connection with Example VI. The prestretched elastomeric member 20 of each segment 810 was maintained in tension by a single rigidifying member 815 secured substantially along the length of the prestretched elastomeric member by heat sealing. These heat sealing bonds were reinforced at points 818 by subjecting the prestretched elastomer 20 and the rigidifying member 815 to a second heat sealing operation oriented perpendicular to the first heat sealing operation to form reinforced heat sealed areas 818 at the ends of each laminate composite structure 810.

Testing:

The disposable baby diaper 850 was put on a baby model 760 using pressure sensitive adhesive tape tabs 735 to hold the diaper on the baby model as it would be in actual use. Each strippable rigidifying member 815 was thereafter grasped at its free end 816 and peeled away from its corresponding prestretched elastomeric member 20. The amount of elasticity required to obtain good diaper fit was easily controlled by the degree to which strippable rigidifying members 815 were peeled from their respective prestretched elastomeric members 20. When the strippable layers 815 were completely removed, the diaper waist band became elastically shirred substantially about its periphery.

EXAMPLE XI

Disposable Diaper Having Peelable Rigidifying Member Applied to Intermediate Carrier Layer The disposable baby diaper of Example XI was made utilizing construction techniques generally similar to those outlined in connection with the diaper of Example X. However, the elastically shirrable segments 810 are applied to an intermediate carrier layer 825 which in turn is applied to the outermost surface of the disposable diaper backsheet 705, again utilizing double faced adhesive tape (not shown). In the Example XI embodiment 950 illustrated in the partially exploded view of FIG. 14, the carrier layer was comprised of 0.001" thick polypropylene film having a width of approximately 2" and a length which extended parallel to and coextensive with the waist band portions of the diaper. The elastically shirrable segments 810 can be affixed to the intermediate carrier layers 825 either prior to or after the carrier layers are secured to the diaper backsheet 705.

Figure 14:
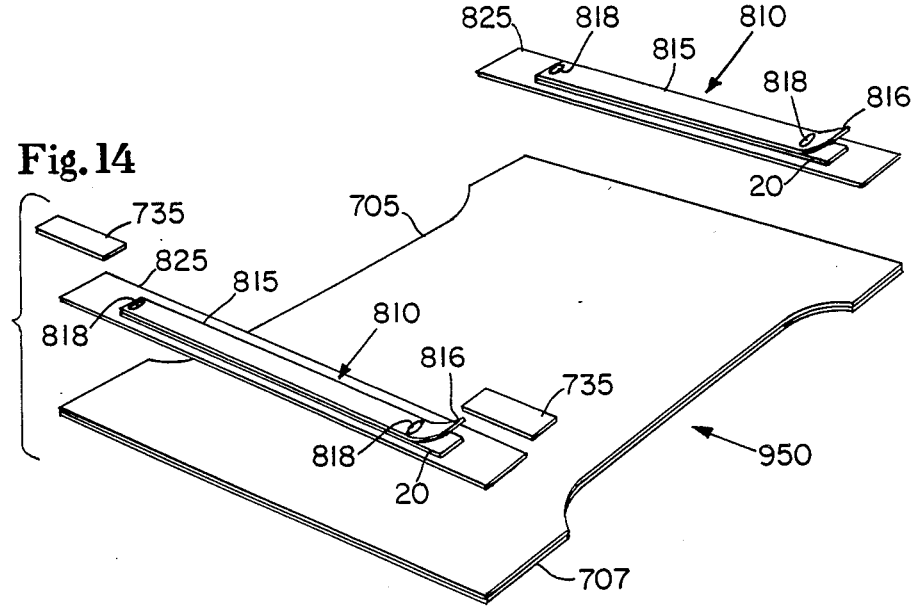
FIG. 14 is a partially exploded view of a diaper generally similar to that shown in FIG. 13, but including an intermediate or carrier layer to which both the elastically shirrable segments and the pressure sensitive adhesive tape tabs are secured.

Pressure sensitive adhesive tape tabs 735 were also applied directly to the exposed surface of the intermediate carrier layer 825 adjacent the lateral edges of the diaper, as generally shown in FIG. 14. When the disposable diaper 950 is applied to the wearer's body, the exposed portions of pressure sensitive adhesive on tape tabs 735 are secured to the exposed portions of carrier layer 825 located on the opposite waist band portion of the diaper.

Since all tensile strain imposed on the waist band portion of the diaper 950 can be confined to the interconnected intermediate carrier layers 825, selecting an intermediate carrier layer 825 which is relatively high in strength, will avoid any damage to the back sheet 705 or the remaining portions of the diaper when it is applied to the wearer. In addition, other properties such as refastenability of the pressure sensitive adhesive tape tabs 735 can be optimized by selecting an exposed surface for the carrier layer 825 which permits a mother to open the diaper and inspect for soiling and thereafter refasten the tape using the same pressure sensitive adhesive on tab 735.

Figure 15:
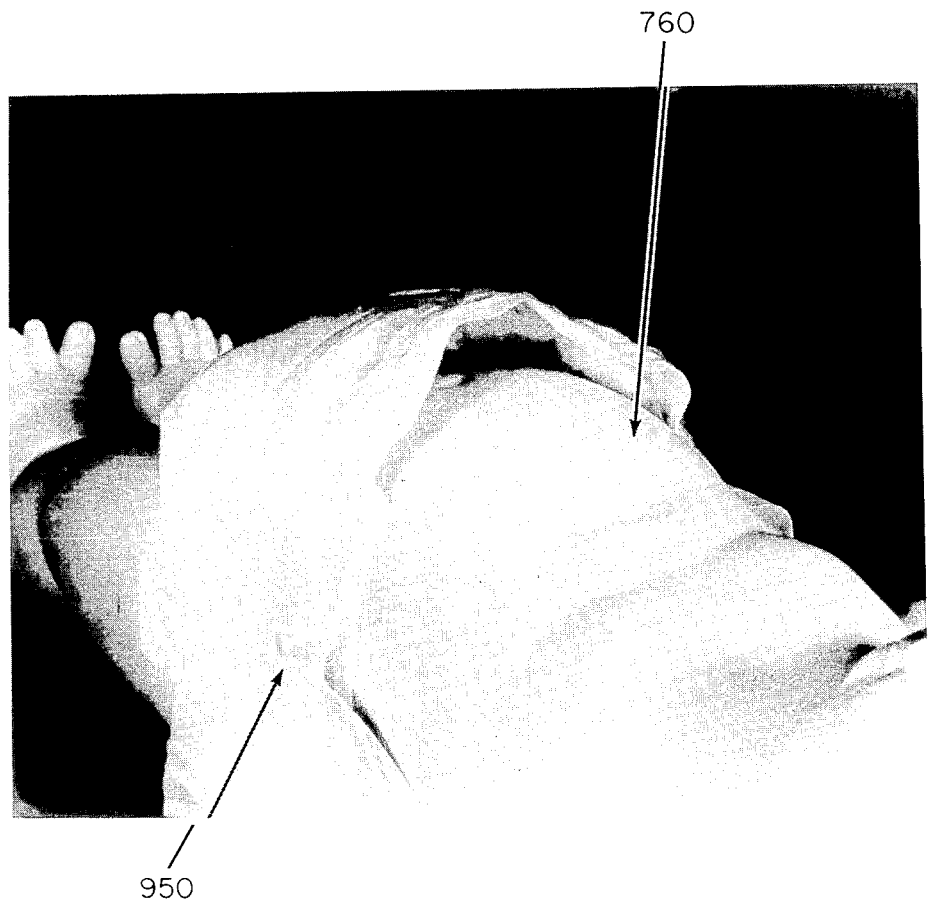
FIG. 15 is a photograph of a diaper of the type generally illustrated in FIG. 14 applied about the torso of a baby model, said diaper being shown prior to the release of tension in either of the elastically shirrable segments contained in the diaper.
Figure 16:
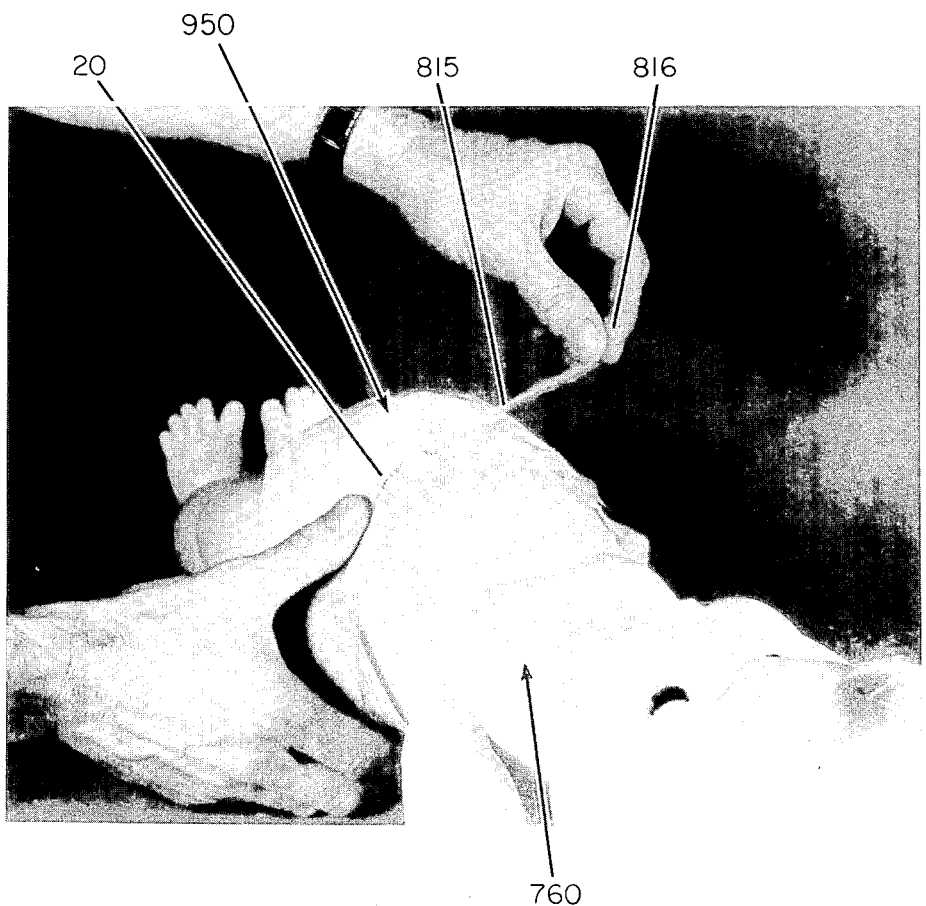
FIG. 16 is a photograph of the diaper generally shown in FIG. 15 demonstrating removal of the peelable rigidifying member from one of the elastically shirrable segments contained in the diaper.
Figure 17:
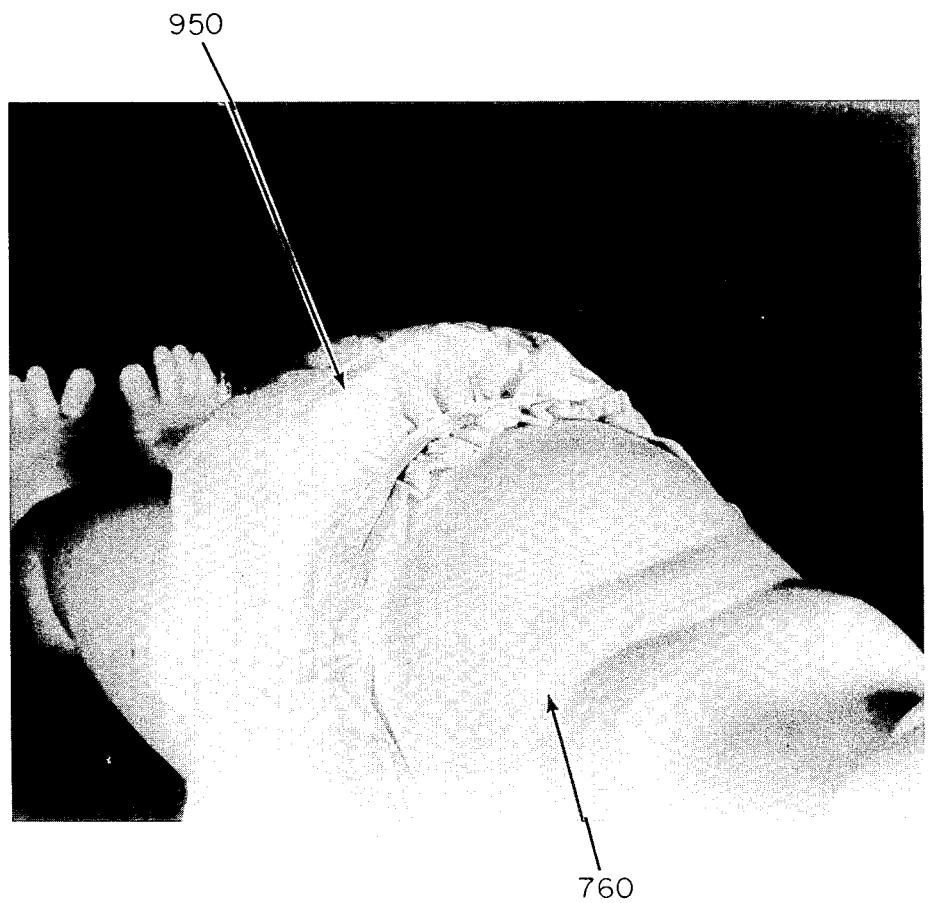
FIG. 17 is a view of the diaper generally shown in FIGS. 15 and 16 after the peelable rigidifying members have been completely removed from the elastically shirrable segments contained in the diaper.

Testing:

The disposable baby diaper 950 was put on a baby model 760 using pressure sensitive adhesive tape tabs 735 to hold the diaper on the baby model as it would be in actual use. The disposable diaper 950 is shown in place, but prior to release of tension in the prestretched elastomeric members included in each elastically shirrable segment 810 in the photograph of FIG. 15. Note the lack of tension about the baby model's waist. The strippable rigidifying member 815 was thereafter grasped at its free end 816 and peeled away from the corresponding prestretched elastomeric member 20, as generally shown in FIG. 16. The amount of elasticity required to obtain good diaper fit was easily controlled by the degree to which the strippable rigidifying members 815 were peeled from their corresponding prestretched elastomeric members 20. When both strippable layers 815 were completely removed, the diaper waist band became elastically shirred, as generally shown in the photograph of FIG. 17. In the event a strippable layer is not completely removed, the peeled portion can be cut or torn from the diaper to preserve a neat appearance.

EXAMPLE XII

Disposable Diaper Having Fold-Over/Flip Release Activation

Figure 13:
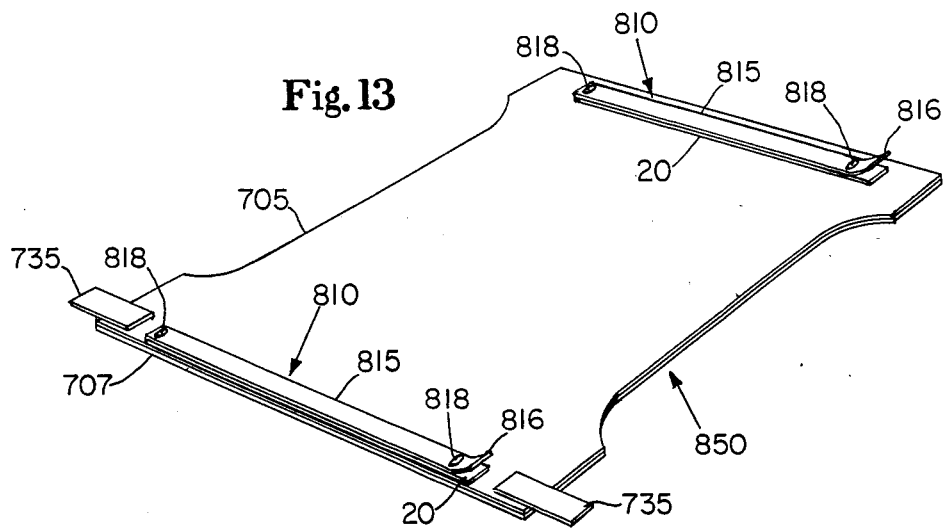
FIG. 13 is a simplified perspective view, taken from the back sheet side, of an alternative disposable diaper wherein elastically shirrable segments having peelable rigidifying layers are mounted to the outermost surface of the diaper back sheet in the waist band portions of the diaper.

The disposable diaper embodiment of Example XII was made utilizing construction techniques generally similar to the embodiment of Example X, while using an elastically shirrable segment of the type described in Example VI A in place of the elastically shirrable segment 810 shown in FIG. 13. An additional layer of two sided adhesive tape was added to the exposed surface of the rigidifying member in the Example XII embodiment.

FIG. 13A shows a disposable diaper 855 employing a pair of identical Example XII elastically shirrable segments 811A and 811B attached to the back sheet 705 of the diaper. The elastically shirrable segment 811(A) is in the unactivated or restrained state while segment 811(B) is shown in its activated or released state, i.e., rigidifying member 857, which remains attached to back sheet 705, has been completely separated from tensioned elastomeric member 858, which has caused the waistband portion of the diaper to which it is secured to elastically shirr.

The unactivated Example XII embodiment of the present invention can be activated by simply unfolding the remaining waistband portion of diaper 855 at area 811(A), which will separate the rigidifying member of the segment from the extended elastomeric member and cause the diaper to shirr in the same manner shown with respect to segment 811(B).

While particular embodiments of the present invention have been illustrated and described, it will be obvious to those skilled in the art that various changes and modifications can be made without departing from the spirit and scope of the invention, and it is intended to cover in the appended claims all such modifications that are within the scope of this invention.

What is claimed is:

1. An unrestrained article including at least one segment which is capable of being elastically shirred subsequent to the manufacture of said article along at least a portion of its length by mechanical manipulation of a predetermined portion thereof, said predetermined mechanically manipulatable portion of said shirrable segment comprising an elastomeric member which prior to mechanical manipulation is maintained in a prestretched and tensioned condition in the desired direction of shirring, the opposed ends of said shirrable segment in said article being interconnected to one another through said prestretched and tensioned elastomeric member, said prestretched and tensioned elastomeric member being secured in fixed relation to at least one rigidifying member to form a composite structure which is strong enough to resist collapse in a direction parallel to the tensile forces acting upon said prestretched and tensioned elastomeric member prior to mechanical manipulation of said predetermined portion of said shirrable segment of said article, said segment of said article being elastically shirrable by mechanically manipulating said predetermined portion of said shirrable segment until movement of said prestretched and tensioned elastomeric member and said rigidifying member relative to one another is effected in the area comprising said composite structure, said relative movement between said prestretched and tensioned elastomeric member and said rigidifying member being sufficient to release the tensile forces in the mechanically manipulated portion of said composite structure, whereby a degree of shirring of said segment will occur in the direction of prestretching of said elastomeric member, said degree of segment shirring being proportional to the extent to which there is relative movement between said prestretched and tensioned elastomeric member and said rigidifying member in the area comprising said composite structure.

2. The article of claim 1, wherein said rigidifying member comprises a layer of pliable material.

3. The article of claim 2, wherein said layer of pliable material comprises a polymeric film.

4. The article of claim 1, wherein said prestretched and tensioned elastomeric member and said rigidifying member are secured in fixed relation to one another by being sealed to one another along the length of said composite structure.

5. The article of claim 4, wherein said seal between said prestretched and tensioned elastomeric member and said rigidifying member comprises a heat seal.

6. The article of claim 4, wherein said seal between said prestretched and tensioned elastomeric member and said rigidifying member comprises an adhesive seal.

7. The article of claim 1, wherein said rigidifying member comprises a brittle material which fractures upon mechanical manipulation of said composite structure to release tension in said prestretched elastomeric member.

8. The article of claim 4, wherein said rigidifying member comprises a ductile material which is peeled from said prestretched and tensioned elastomeric member to release tension therein.

9. The article of claim 1, wherein said rigidifying material comprises a fluid which has been allowed to dry.

10. The article of claim 1, wherein at least a portion of said prestretched and tensioned elastomeric member in said elastically shirrable segment is secured directly to said article.

11. The article of claim 1, wherein said elastically shirrable segment includes a composite structure formed by said prestretched and tensioned elastomeric member and said rigidifying member along substantially its entire length.

12. An article including at least one segment which is capable of being elastically shirred along at least a portion of its length by mechanical manipulation of a predetermined portion thereof, said predetermined mechanically manipulatable portion of said shirrable segment comprising an elastomeric member which prior to mechanical manipulation is maintained in a prestretched and tensioned condition in the desired direction of shirring, the opposed ends of said shirrable segment in said article being interconnected to one another through said prestretched and tensioned elastomeric member, said prestretched and tensioned elastomeric member being secured in fixed relation to a pair of rigidifying members located on opposed surfaces of said prestretched and tensioned elastomeric member to form a composite structure which is strong enough to resist collapse in a direction parallel to the tensile forces acting upon said prestretched and tensioned elastomeric member prior to mechanical manipulation of said predetermined portion of said shirrable segment of said article, said segment of said article being elastically shirrable by mechanically manipulating said predetermined portion of said shirrable segment until movement of said prestretched and tensioned elastomeric member and said rigidifying member relative to one another is effected in the area comprising said composite structure, said relative movement between said prestretched and tensioned elastomeric member and said rigidifying member being sufficient to release the tensile forces in the mechanically manipulated portion of said composite structure, whereby a degree of shirring of said segment will occur in the direction of prestretching of said elastomeric member, said degree of segment shirring being proportional to the extent to which there is relative movement between said prestretched and tensioned elastomeric member and said rigidifying member in the area comprising said composite structure.

13. The article of claim 12, wherein said rigidifying members are comprised of a pliable material and are sealed to one another, but not to said prestretched elastomeric member along the length of said composite structure, said prestretched and tensioned elastomeric member being restrained from retracting along the length of said rigidifying members by securement at the opposing ends of said rigidifying members.

14. The article of claim 13, wherein securement of said prestretched and tensioned elastomeric member at the opposing ends of said rigidifying members comprises a seal between said elastomeric member and said rigidifying members.

15. The article of claim 14, wherein said seal between said elastomeric member and said rigidifying members comprises a heat seal.

16. The article of claim 13, wherein a substantially untensioned portion of said elastomeric member extends beyond each opposing end of said rigidifying members, said substantially untensioned portions of said elastomer member being secured directly to said article, whereby release of tension in said prestretched and tensioned portion of said elastomeric member intermediate said points of attachment to said article elastically shirrs said article intermediate said points of attachment.

17. An unrestrained article including at least one segment which will automatically elastically shirr without external heating along a predetermined portion of its length subsequent to the manufacture of said article, said predetermined portion of said shirrable segment comprising an elastomeric member which prior to and during manufacture of said article is maintained in a prestretched and tensioned condition in the desired direction of shirring, the opposed ends of said shirrable segment in said article being interconnected to one another through said prestretched and tensioned elastomeric member, said prestretched and tensioned elastomeric member being secured in substantially fixed relation to at least one rigidifying member to form a composite structure which is strong enough to resist collapse in a direction parallel to the tensile forces acting upon said prestretched and tensioned elastomeric member at least until the manufacture of said article has been completed, said segment of said article being automatically elastically shirred by self-induced relative movement between said prestretched and tensioned elastomeric member and said rigidifying member at a rate response to the coming into play of inherent physical characteristics for which the elastomeric and rigidifying member components of the composite were considered and deliberately selected, whereby a degree of shirring of said segment will occur in the direction of prestretching of said elastomeric member, said degree of segment shirring being proportional to the extent to which there is relative movement between said prestretched and tensioned elastomeric member and said rigidifying member in the area comprising said composite structure.

18. The article of claim 17, wherein said rigidifying member comprises a layer of pliable material.

19. The article of claim 18, wherein said layer of pliable material comprises a polymeric film.

20. The article of claim 18, wherein said prestretched and tensioned elastomeric member and said rigidifying member are secured in fixed relation to one another along their length by means of an adhesive which will creep when subjected to stress.

21. The article of claim 20, wherein said adhesive is pressure sensitive.

22. An article inlcuding at least one segment which will automatically elastically shirr without external heating along a predetermined portion of its length subsequent to the manufacture of said article, said predetermined portion of said shirrable segment comprising an elastomeric member which prior to and during manufacture of said article is maintained in a prestretched and tensioned condition in the desired direction of shirring, the opposed ends of said shirrable segment in said article being interconnected to one another through said prestretched and tensioned elastomeric member, said prestretched and tensioned elastomeric member being secured in substantially fixed relation along its length to at least one rigidifying member comprising a layer of pliable, pressure sensitive tape, said tape having a pressure sensitive adhesive which will creep when subjected to stress, said prestretched and tensioned elastomeric member and said rigidifying member forming a composite structure which is strong enough to resist collapse in a direction parallel to the tensile forces acting upon said prestretched and tensioned elastomeric member at least until the manufacture of said article has been completed, said segment of said article being automatically elastically shirred by self-induced relative movement between said prestretched and tensioned elastomeric member and said rigidifying member at a rate responsive to the coming into play of inherent physical characteristics for which the elastomeric and rigidifying member components of the composite were considered and deliberately selected, whereby a degree of shirring of said segment will occur in the direction of prestretching of said elastomeric member, said degree of segment shirring being proportional to the extent to which there is relative movement between said prestretched and tensioned elastomeric member and said rigidifying member in the area comprising said composite structure.

23. An unrestrained elastically shirrable segment for attachment to an article to be elastically shirred subsequent to manufacture of said article, said segment being capable of being elastically shirred along at least a portion of its length by mechanical manipulation of a predetermined portion thereof, said predetermined mechanically manipulatable portion of said shirrable segment comprising an elastomeric member which prior to mechanical manipulation is maintained in a prestretched and tensioned condition in the desired direction of shirring, the opposed ends of said shirable segment being interconnected to one another through said prestretched and tensioned elastomeric member, said prestretched and tensioned elastomeric member being secured in fixed relation to at least one rigidifying member to form a composite structure which is strong enough to resist collapse in a direction parallel to the tensile forces acting upon said prestretched and tensioned elastomeric member prior to mechanical manipulation of said predetermined portion of said shirrable segment, said segment having the capability of being elastically shirred after said segment is attached to said article by mechanically manipulating said predetermined portion of said shirrable segment until movement of said prestretched and tensioned elastomeric member and said rigidifying member relative to one another is effected in the area comprising said composite structure, said relative movement between said prestretched and tensioned elastomeric member and said rigidifying member being sufficient to release the tensile forces in the mechanically manipulated portion of said composite structure, whereby a degree of shirring of said segment will occur in the direction of prestretching of said elastomeric member, said degree of segment shirring being proportional to the extent to which there is relative movement between said prestretched and tensioned elastomeric member and said rigidifying member in the area comprising said composite structure.

24. The segment of claim 23, wherein said rigidifying member comprises a layer of pliable material.

25. The segment of claim 24, wherein said layer of pliable material comprises a polymeric film.

26. The segment of claim 23, wherein said prestretched and tensioned elastomeric member and said rigidifying member are secured in fixed relation to one another by being sealed to one another along the length of said composite structure.

27. The segment of claim 26, wherein said seal between said prestretched and tensioned elastomeric member and said rigidifying member comprises a heat seal.

28. The segment of claim 26, wherein said seal between said prestretched and tensioned elastomeric member and said rigidifying member comprises an adhesive seal.

29. The segment of claim 23, wherein said rigidifying member comprises a brittle material which fractures upon mechanical manipulation of said composite structure to release tension in said prestretched elastomeric member.

30. The segment of claim 26, wherein said rigidifying member comprises a ductile material which is peeled from said prestretched and tensioned elastomeric member to release tension therein.

31. The segment of claim 23, wherein said rigidifying material comprises a fluid which has been allowed to dry.

32. The segment of claim 23, wherein at least a portion of said prestretched and tensioned elastomeric member in said elastically shirrable segment is exposed for securement directly to said article.

33. The segment of claim 23, wherein said composite structure formed by said prestretched and tensioned elastomeric member and said rigidifying member extends along substantially the entire length of said segment.

34. An elastically shirrable segment for attachment to an article to be elastically shirred, said segment being capable of being elastically shirred along at least a portion of its length by mechanical manipulation of a predetermined portion thereof, said predetermined mechanically manipulatable portion of said shirrable segment comprising an elastomeric member which prior to mechanical manipulation is maintained in a prestretched and tensioned condition in the desired direction of shirring, the opposed ends of said shirrable segment being interconnected to one another through said prestretched and tensioned elastomeric member, said prestretched and tensioned elastomeric member being secured in fixed relation to a pair of rigidifying members located on opposed surfaces of said prestretched and tensioned elastomeric member to form a composite structure which is strong enough to resist collapse in a direction parallel to the tensile forces acting upon said prestretched and tensioned elastomeric member prior to mechanical manipulation of said predetermined portion of said shirrable segment, said segment having the capability of being elastically shirred after said segment is attached to said article by mechanically manipulating said predetermined portion of said shirrable segment until movement of said prestretched and tensioned elastomeric member and said rigidifying members relative to one another is effected in the area comprising said composite structure, said relative movement between said prestretched and tensioned elastomeric member and said rigidifying members being sufficient to release the tensile forces in the mechanically manipulated portion of said composite structure, whereby a degree of shirring of said segment will occur in the direction of prestretching of said elastomeric member, said degree of segment shirring being proportional to the extent to which there is relative movement between said prestretched and tensioned elastomeric member and said rigidifying members in the area comprising said composite structure.

35. The segment of claim 34, wherein said rigidifying members are comprised of a pliable material and are sealed to one another, but not to said prestretched elastomeric member along the length of said composite structure, said prestretched and tensioned elastomeric member being restrained from retracting along the length of said rigidifying members by securement at the opposing ends of said rigidifying members.

36. The segment of claim 35, wherein securement of said prestretched and tensioned elastomeric member at the opposing ends of said rigidifying members comprises a seal between said elastomeric member and said rigidifying members.

37. The segment of claim 36, wherein said seal between said elastomeric member and said rigidifying members comprises a heat seal.

38. The segment of claim 35, wherein a substantially untensioned portion of said elastomeric member extends beyond each opposing end of said rigidifying members, said substantially untensioned portions of said elastomeric member being exposed for securement directly to said article.

39. An unrestrained elastically shirrable segment for attachment to an article to be elastically shirred subsequent to the manufacture of said article, said segment exhibiting an ability to automatically elastically shirr without external heating along a predetermined portion of its length subsequent to its attachment to said article, said predetermined portion of said shirrable segment comprising an elastomeric member which prior to and during manufacture of said article is maintained in a prestretched and tensioned condition in the desired direction of shirring, the opposed ends of said shirrable segment being interconnected to one another through said prestretched and tensioned elastomeric member, said prestretched and tensioned elastomeric member being secured in substantially fixed relation to at least one rigidifying member to form a composite structure which is strong enough to resist collapse in a direction parallel to the tensile forces acting upon said prestretched and tensioned elastomeric member at least until the attachment of said segment to said article has been completed, said segment being automatically elastically shirrable by self-induced relative movement between said prestretched and tensioned elastomeric member and said rigidifying member at a rate responsive to the coming into play of inherent physical characteristics for which the elastomeric and rigidifying member components of the composite were considered and deliberately selected, whereby a degree of shirring of said segment will occur in the direction of prestretching of said elastomeric member, said degree of segment shirring being proportional to the extent to which there is relative movement between said prestretched and tensioned elastomeric member and said rigidifying member in the area comprising said composite structure.

40. The segment of claim 39, wherein said rigidifying member comprises a layer of pliable material.

41. The segment of claim 40, wherein said layer of pliable material comprises a polymeric film.

42. The segment of claim 40, wherein said prestretched and tensioned elastomeric member and said rigidifying member are secured in fixed relation to one another along their length by means of an adhesive which will creep when subjected to stress.

43. The segment of claim 42, wherein said adhesive is pressure sensitive.

44. An elastically shirrable segment for attachment to an article to be elastically shirred, said segment exhibiting an ability to automatically elastically shirr without external heating along a predetermined portion of its length subsequent to its attachment to said article, said predetermined portion of said shirrable segment comprising an elastomeric member which prior to and during manufacture of said article is maintained in a prestretched and tensioned condition in the desired direction of shirring, the opposed ends of said shirrable segment being interconnected to one another through said prestretched and tensioned elastomeric member, said prestretched and tensioned elastomeric member being secured in substantially fixed relation along its length to at least one rigidifying member comprising a layer of pliable, pressure sensitive tape said tape having a pressure sensitive adhesive which will creep when subjected to stress, said prestretched and tensioned elastomeric member and said rigidifying member forming a composite structure which is strong enough to resist collapse in a direction parallel to the tensile forces acting upon said prestretched and tensioned elastomeric member at least until the attachment of said segment to said article has been completed, said segment being automatically elastically shirred by self-induced relative movement between said prestretched and tensioned elastomeric member and said rigidifying member at a rate responsive to the coming into play of inherent physical characteristics for which the elastomeric and rigidifying member components of the composite were considered and deliberately selected, whereby a degree of shirring of said segment will occur in the direction of prestretching of said elastomeric member, said degree of segment shirring being proportional to the extent to which there is relative movement between said prestretched and tensioned elastomeric member and said rigidifying member in the area comprising said composite structure.

45. A method for making an elastically shirrable segment for attachment to an article to be elasticized subsequent to the manufacture of said article, said method comprising the steps of:
(a) subjecting an elastomeric member to tension in at least one direction; and
(b) securing said prestretched and tensioned elastomeric member in fixed relation to at least one rigidifying member to form a composite structure which is strong enough to resist collapse in a direction parallel to the tensile forces acting upon said prestretched and tensioned elastomeric member, but which when mechanically manipulated will permit said prestretched and tensioned elastomeric member and said rigidifying member to undergo movement relative to one another in the area comprising said composite structure, said relative movement being sufficient to release the tensile forces in at least a portion of said composite structure, whereby a degree of segment shirring will occur in the direction of prestretching of said elastomeric member, said degree of shirring being porportional to the extent to which there is relative movement between said prestretched and tensioned elastomeric member and said rigidifying member in the area comprising said composite structure.

46. A method for making an article including an elasticizable segment which can be elasticized subsequent to the manufacture of said article, said method comprising the steps of:
(a) subjecting an elastomeric member to tension in at least one direction;
(b) securing said prestretched and tensioned elastomeric member in fixed relation to at least one rigidifying member to form a composite structure which is strong enough to resist collapse in a direction parallel to the tensile forces acting upon said prestretched and tensioned elastomeric member until subjecting said composite to mechanical manipulation; and
(c) securing said composite structure while it is in a substantially untensioned condition to the portion of said article to be elasticized so that the tensile forces acting upon said prestretched and tensioned elastomeric member are aligned in the desired direction of article shirring, whereby upon mechanical manipulation of said composite structure said prestretched and tensioned elastomeric member and said rigidifying member will undergo movement relative to one another in the area comprising said composite structure, said relative movement being sufficient to release the tensile forces in at least a portion of said composite structure, whereby a degree of article shirring will occur in the direction of prestretching of said elastomeric member, said degree of shirring being proportional to the extent to which there is relative movement between said prestretched and tensioned elastomeric member and said rigidifying member in the area comprising said composite structure.

47. A method for elasticizing a predetermined portion of an article subsequent to the manufacture of said article, said method comprising the steps of:
(a) subjecting an elastomeric member to tension in at least one direction;
(b) securing said prestretched and tensioned elastomeric member in fixed relation to at least one rigidifying member to form a composite structure which is strong enough to resist collapse in a direction parallel to the tensile forces acting upon said prestretched and tensioned elastomeric member;
(c) securing said composite structure while it is in a substantially untensioned condition to the portion of said article to be elasticized so that the tensile forces acting upon said prestretched and tensioned elastomeric member are aligned in the desired direction of article shirring; and
(d) causing said prestretched and tensioned elastomeric member and said rigidifying member to undergo movement relative to one another in the area comprising said composite structure subsequent to the manufacture of said article either by mechanically manipulating said composite structure or permitting to come into play without external heating the inherent physical characteristics for which said elastomeric and rigidifying members were considered and deliberately selected as composite components, said relative movement being sufficient to release the tensile forces in at least a portion of said composite structure, whereby a degree of article shirring will occur in the direction of prestretching of said elastomeric member, said degree of shirring being proportional to the extent to which there is relative movement between said prestretched and tensioned elastomeric member and said rigidifying member in the area comprising said composite structure.

48. The method of claim 47, wherein said prestretched and tensioned elastomeric member and said rigidifying member are caused to undergo movement relative to one another by mechanically manipulating said composite structure.

49. An article including at least one segment which is capable of being elastically shirred along at least a portion of its length by mechanical manipulation of a predetermined portion thereof, said predetermined mechanically manipulatable portion of said shirrable segment comprising an elastomeric member which prior to mechanical manipulation is maintained in a prestretched and tensioned condition in the desired direction of shirring, said prestretched and tensioned elastomeric member having at least one irregular surface, the opposed ends of said shirrable segment in said article being interconnected to one another through said prestretched and tensioned elastomeric member, said prestretched and tensioned elastomeric member being secured in fixed relation to at least one rigidifying member which also exhibits at least one irregular surface, said prestretched and tensioned elastomeric member and said rigidifying member being so oriented that said irregular surface on said elastomeric member and said irregular surface on said rigidifying member engage one another to form a composite structure which is strong enough to resist collapse in a direction parallel to the tensile forces acting upon said prestretched and tensioned elastomeric member until movement of said prestretched and tensioned elastomeric member and said rigidifying member relative to one another is effected by mechanical manipulation of said composite structure, said relative movement between said prestretched and tensioned elastomeric member and said rigidifying member being sufficient to release the tensile forces in the mechanically manipulated portion of said composite structure, whereby a degree of shirring of said segment will occur in the direction of prestretching of said elastomeric member, said degree of segment shirring being proportional to the extent to which there is relative movement between said prestretched and tensioned elastomeric member and said rigidifying member in the area comprising said composite structure.

50. The article of claim 49, wherein said irregular surface exhibited by said rigidifying member comprises a multiplicity of relief sites and said irregular surface on said prestretched and tensioned elastomeric member comprises a multiplicity of raised areas which extend into said multiplicity of relief sites in said rigidifying member.

51. The article of claim 49, wherein said irregular surface exhibited by said rigidifying member comprises a multiplicity of raised areas and said irregular surface on said prestretched and tensioned elastomeric member comprises a multiplicity of relief sites which receive said multiplicity of raised areas in said rigidifying member.

52. The article of claim 50 or claim 51, wherein said relief sites and said raised areas are substantially complementary to one another when the irregular surfaces on said tensioned elastomeric member and said rigidifying member are placed in contact with one another.

53. The article of claim 52, wherein said rigidifying member and said tensioned elastomeric member in said segment are each secured to different portions of said article, said article being folded upon itself so that said irregular surface on said tensioned elastomeric member and said irregular surface on said rigidifying member engage one another in superposed relation, said segment being capable of mechanical manipulation to elastically shirr said article by unfolding the superposed portions of said article from one another, thereby separating said tensioned elastomeric member from said rigidifying member.

54. An elastically shirrable segment for attachment to an article to be elastically shirred, said segment being capable of being elastically shirred along at least a portion of its length by mechanical manipulation of a predetermined portion thereof, said predetermined mechanically manipulatable portion of said shirrable segment comprising an elastomeric member which prior to mechanical manipulation is maintained in a prestretched and tensioned condition in the desired direction of shirring, said prestretched and tensioned elastomeric member having at least one irregular surface the opposed ends of said shirrable segment being interconnected to one another through said prestretched and tensioned elastomeric member, said prestretched and tensioned elastomeric member being secured in fixed relation to at least one rigidifying member which also exhibits at least one irregular surface, said prestretched and tensioned elastomeric member and said rigidifying member being so oriented that said irregular surface on said elastomeric member and said irregular surface on said rigidifying member engage one another to form a composite structure which is strong enough to resist collapse in a direction parallel to the tensile forces acting upon said prestretched and tensioned elastomeric member prior to mechanical manipulation of said portion of said shirrable segment, said segment having the capability of being elastically shirred after said segment is attached to said article by mechanically manipulating said portion of said shirrable segment until movement of said prestretched and tensioned elastomeric member and said rigidifying member relative to one another is effected in the area comprising said composite structure, said relative movement between said prestretched and tensioned elastomeric member and said rigidifying member being sufficient to release the tensile forces in the mechanically manipulated portion of said composite structure, whereby a degree of shirring of said segment will occur in the direction of prestretching of said elastomeric member, said degree of segment shirring being proportional to the extent to which there is relative movement between said prestretched and tensioned elastomeric member and said rigidifying member in the area comprising said composite structure.

55. The elastically shirrable segment of claim 54, wherein said irregular surface exhibited by said rigidifying member comprises a multiplicity of relief sites and said irregular surface on said prestretched and tensioned elastomeric member comprises a multiplicity of raised areas which extend into said multiplicity of relief sites in said rigidifying member.

56. The elastically shirrable segment of claim 54, wherein said irregular surface exhibited by said rigidifying member comprises a multiplicity of raised areas and said irregular surface on said prestretched and tensioned elastomeric member comprises a multiplicity of relief sites which receive said multiplicity of raised areas in said rigidifying member.

57. The elastically shirrable segment of claim 55 or claim 56, wherein said relief sites and said raised areas are substantially complementary to one another when the irregular surfaces on said tensioned elastomeric member and said rigidifying member are placed in contact with one another.

58. An article including at least one segment which is capable of being elastically shirred along at least a portion of its length by mechanically acting upon a predetermined portion thereof, said predetermined portion of said shirrable segment comprising an elastomeric member which prior to being mechanically acted upon is maintained in a longitudinally extended condition in the desired direction of shirring, the opposed ends of said shirrable segment in said article being interconnected to one another through said longitudinally extended elastomeric member, said longitudinally extended elastomeric member being secured in fixed relation to an encapsulating restraint member while said elastomeric member is in a prestretched and tensioned condition, said encapsulating restraint member being strong enough to maintain said longitudinally extended elastomeric member in a state of compression sufficient to prevent said longitudinally extended elastomeric member from expanding in any direction perpendicular to the desired direction of shirring until said segment of said article is mechanically acted upon by rupturing said encapsulating restraint member along said predetermined portion of said segment to effect release of the compressive force acting upon said longitudinally extended elastomeric member, thereby simultaneously restoring and releasing the tensile forces in that portion of the longitudinally extended elastomeric member which has been freed of restraint and effecting a degree of shirring of said segment of said article along the length of said longitudinally extended elastomeric member, said degree of segment shirring being proportional to the extent to which said encapsulating restraint member is ruptured along the length of said segment.

59. The article of claim 58, wherein said encapsulating restraint member comprise a layer of pliable material wrapped about and secured in position along the length of said longitudinally extended elastomeric member while said elastomeric member is in a prestretched and tensioned condition.

60. The article of claim 59, wherein said shirrable segment includes means for rupturing said encapsulating restrain member.

61. The article of claim 60, wherein said means for rupturing said encapsulating restrain member comprises a filament secured intermediate said longitudinally extended elastomeric member and the interior of said encapsulating restraint member, said filament having at least one end protruding beyond said encapsulating restrain member to facilitate easy grasping and pulling to rupture said encapsulating restraint member.

62. An elastically shirrable segment for attachment to an article to be elastically shirred, said segment being capable of being elastically shirred along at least a portion of its length by mechanically acting upon a predetermined portion thereof said predetermined portion of said shirrable segment comprising an elastomeric member which prior to being mechanically acted upon is maintained in a longitudinally extended condition in the desired direction of shirring, the opposed ends of said shirrable segment being interconnected to one another through said longitudinally extended elastomeric member, said longitudinally extended elastomeric member being secured in fixed relation to an encapsulating restraint member while said elastomeric member is in a prestretched and tensioned condition, said encapsulating restraint member being strong enough to maintain said longitudinally extended elastomeric member in a state of compression sufficient to prevent said longitudinally extended elastomeric member from expanding in any direction perpendicular to the desired direction of shirring until said segment is mechanically acted upon by rupturing said encapsulating restraint member along said predetermined portion of said shirrable segment to effect release of the compressive force acting upon said longitudinally extended elastomeric member, thereby simultaneously restoring and releasing the tensile forces in that portion of the longitudinally extended elastomeric member which has been freed of restraint and effecting a degree of shirring of said segment along the length of said longitudinally extended elastomeric member, said degree of segment shirring being proportional to the extent to which said encapsulating restraint member is ruptured along the length of said segment.

63. The elastically shirrable segment of claim 62, wherein said encapsulating restraint member comprises a layer of pliable material wrapped about and secured in position along the length of said longitudinally extended elastomeric member while said elastomeric member is in a prestretched and tensioned condition.

64. The elastically shirrable segment of claim 63, wherein said shirrable segment includes means for rupturing said encapsulating restraint member.

65. The elastically shirrable segment of claim 64, wherein said means for rupturing said encapsulating restraint member comprises a filament secured intermediate said longitudinally extended elastomeric member and the interior of said encapsulating restraint member, said filament having at least one end protruding beyond said encapsulating restraint member to facilitate easy grasping and pulling to rupture said encapsulating restraint member.

66. A method for making an elastically shirrable segment for attachment to an article to be elasticized, said method comprising the steps of:
(a) subjecting an elastomeric member to tension in at least one direction, said tensioned elastomeric member exhibiting at least one irregular surface; and
(b) securing said prestretched and tensioned elastomeric member in fixed relation to at least one rigidifying member which also exhibits at least one irregular surface by engaging said irregular surface on said prestretched and tensioned elastomeric member and said irregular surface on said rigidifying member with one another to form a composite structure which is strong enough to resist collapse in a direction parallel to the tensile forces acting upon said prestretched and tensioned elastomeric member until subjecting said composite to mechanical manipulation, but which when mechanically manipulated will permit said prestretched and tensioned elastomeric member and said rigidifying member to undergo movement relative to one another in the area comprising said composite structure, said relative movement being sufficient to release the tensile forces in at least a portion of said composite structure, whereby a degree of segment shirring will occur in the direction of prestretching of said elastomeric member, said degree of shirring being proportional to the extent to which there is relative movement between said prestretched and tensioned elastomeric member and said rigidifying member in the area comprising said composite structure.

67. A method for making an article including an elasticizable segment, said method comprising the steps of:
(a) subjecting an elastomeric member to tension in at least one direction, said tensioned elastomeric member exhibiting at least one irregular surface;
(b) securing said prestretched and tensioned elastomeric member in fixed relation to at least one rigidifying member which also exhibits at least one irregular surface by engaging said irregular surface on said prestretched and tensioned elastomeric member and said irregular surface on said rigidifying member with one another to form a composite structure which is strong enough to resist collapse in a direction parallel to the tensile forces acting upon said prestretched and tensioned elastomeric member until subjecting said composite to mechanical manipulation; and
(c) securing said composite structure while it is in a substantially untensioned condition to the portion of said article to be elasticized so that the tensile forces acting upon said prestretched and tensioned elastomeric member are aligned in the desired direction of article shirring, whereby upon mechanical manipulation of said composite structure said prestretched and tensioned elastomeric member and said rigidifying member will undergo movement relative to one another in the area comprising said composite structure, said relative movement being sufficient to release the tensile forces in at least a portion of said composite structure, whereby a degree of article shirring will occur in the direction of prestretching of said elastomeric member, said degree of shirring being proportional to the extent to which there is relative movement between said prestretched and tensioned elastomeric member and said rigidifying member in the area comprising said composite structure.

68. A method for elasticizing a predetermined portion of an article, said method comprising the steps of:
(a) subjecting an elastomeric member to tension in at least one direction, said tensioned elastomeric member exhibiting at least one irregular surface;
(b) securing said prestretched and tensioned elastomeric member in fixed relation to at least one rigidifying member which also exhibits at least one irregular surface by engaging said irregular surface on said prestretched and tensioned elastomeric member and said irregular surfacee on said rigidifying member with one another to form a composite structure which is strong enough to resist collapse in a direction parallel to the tensile forces acting upon said prestretched and tensioned elastomeric member until subjecting said composite to mechanical manipulation;
(c) securing said composite structure while it is in a substantially untensioned condition to the portion of said article to be elasticized so that the tensile forces acting upon said prestretched and tensioned elastomeric member are aligned in the desired direction of article shirring; and
(d) subjecting said composite structure to mechanical manipulation to disengage said irregular surface on said tensioned elastomeric member from said irregular surface on said rigidifying member, thereby causing said prestretched and tensioned elastomeric member and said rigidifying member to undergo movement relative to one another in the area comprising said composite structure, said relative movement being sufficient to release the tensile forces in at least a portion of said composite structure, whereby a degree of article shirring will occur in the direction of prestretching of said elastomeric member, said degree of shirring being proportional to the extent to which there is relative movement between said prestretched and tensioned elastomeric member and said rigidifying member in the area comprising said composite structure.

69. A method for making an elastically shirrable segment for attachment to an article to be elasticized, said method comprising the steps of:
(a) subjecting an elastomeric member to tension in at least one direction; and
(b) securing said prestretched and tensioned elastomeric member in fixed relation to an encapsulating restraint member while said elastomeric member is in a prestretched condition to form a composite structure, said encapsulating restraint member being strong enough to maintain said longitudinally extended elastomeric member in a state of compression sufficient to prevent said longitudinally extended elastomeric member from expanding in any direction perpendicular to the desired direction of shirring prior to mechanical manipulation thereof, but capable of being rupture by mechanical manipulation to effect release of the compressive forces acting upon said longitudinally extended elastomeric member, thereby simultaneously restoring and releasing the tensile forces in that portion of the longitudinally extended elastomeric member which has been freed of restraint and effecting a degree of shirring of said segment along the length of said longitudinally extended elastomeric member, said degree of segment shirring being proportional to the extent to which said encapsulating restrain member is ruptured along the length of said segment.

70. The method of claim 69, wherein the step of securing said prestretched and tensioned elastomeric member in fixed relation to said encapsulating restraint member comprises wrapping a layer of pliable material about and securing it in position along the length of said longitudinally extended elastomeric member while said elastomeric member is in a prestretched and tensioned condition.

71. The method of claim 70, including the step of securing a filament intermediate said longitudinally extended elastomeric member and the interior of said encapsulating restraint member, said filament having at least one end protruding beyond said encapsulating restraint member to facilitate easy grasping and pulling to rupture said encapsulating restraint member.

* * * * *

UNITED STATES PATENT AND TRADEMARK OFFICE
CERTIFICATE OF CORRECTION

PATENT NO. : 4,908,247

DATED : March 13, 1990

INVENTOR(S) : James C. Baird, Thurman J. Koger, II, Delmar R. Muckenfuhs and Milton D. Spahni It is certified that error appears in the above-identified patent and that said Letters Patent is hereby corrected as shown below:

On the title page:
In REFERENCES CITED section, FOREIGN PATENT DOCUMENTS, "WO86/00676" should read -- WO80/00676 -- .

In the ABSTRACT, line 8, "monomer" should read -- member -- .

Column 4, line 14, "it" should read -- its -- .

Column 4, line 61, "regidifying" should read -- rigidifying -- .

Column 10, line 5, after "restraint" insert -- member -- .

Column 10, line 37, "rigidying" should read -- rigidifying -- .

Column 15, line 33, after "Midland" insert -- , -- .

Column 15, line 40, after "1/2" insert -- " -- .

Column 17, line 36, "then" should read -- when -- .

Column 18, line 13, after "1/8" insert -- " -- .

Column 18, line 20, "of" should read -- or -- .

Column 19, line 36, "dimensin" should read -- dimension -- .

Column 20, line 48, "ong" should read -- long -- .

Column 22, line 55, "Windor" should read -- Windsor -- .

Column 23, line 42, "procedur" should read -- procedure -- .

Column 23, line 48, "Proctor" should read -- Procter -- .

Column 28, line 34, "elastomer" should read -- elastomeric -- .

Column 28, line 62, "response" should read -- responsive -- .

Column 36, line 68, "comprise" should read -- comprises -- .

Column 37, line 7, "restrain" should read -- restraint -- .

UNITED STATES PATENT AND TRADEMARK OFFICE
CERTIFICATE OF CORRECTION

PATENT NO. : 4,908,247

DATED : March 13, 1990

INVENTOR(S) : James C. Baird, Thurman J. Koger, II, Delmar R. Muckenfuhs, Milton D. Spahni It is certified that error appears in the above-identified patent and that said Letters Patent is hereby corrected as shown below:

Column 37, line 9, "restrain" should read -- restraint -- .

Column 37, line 14, "restrain" should read -- restraint -- .

Column 39, line 13, "surfacee" should read -- surface -- .

Column 40, line 17, "rupture" should read -- ruptured -- .

Column 40, line 28, "restrain" should read -- restraint -- .

Signed and Sealed this

Seventh Day of April, 1992

Attest:

HARRY F. MANBECK, JR.

Attesting Officer      Commissioner of Patents and Trademarks